US008910919B2

(12) United States Patent
Bonnal et al.

(10) Patent No.: US 8,910,919 B2
(45) Date of Patent: Dec. 16, 2014

(54) SELECTIVELY SEALABLE MALE NEEDLELESS CONNECTORS AND ASSOCIATED METHODS

(75) Inventors: Olivier Bonnal, Melsungen (DE); Juergen Fuchs, Bad Emstal (DE); Andreas Katerkamp, Melsungen (DE)

(73) Assignee: B. Braun Melsungen AG, Melsungen (DE)

( * ) Notice: Subject to any disclaimer, the term of this patent is extended or adjusted under 35 U.S.C. 154(b) by 221 days.

(21) Appl. No.: 13/392,642

(22) PCT Filed: Sep. 3, 2010

(86) PCT No.: PCT/US2010/047898
§ 371 (c)(1),
(2), (4) Date: Apr. 18, 2012

(87) PCT Pub. No.: WO2011/029056
PCT Pub. Date: Mar. 10, 2011

(65) Prior Publication Data
US 2012/0192968 A1 Aug. 2, 2012

Related U.S. Application Data

(60) Provisional application No. 61/239,913, filed on Sep. 4, 2009, provisional application No. 61/242,281, filed on Sep. 14, 2009, provisional application No. 61/257,338, filed on Nov. 2, 2009.

(51) Int. Cl.
*F16K 51/00* (2006.01)
*A61M 39/26* (2006.01)
*A61M 39/10* (2006.01)

(52) U.S. Cl.
CPC .......... *A61M 39/26* (2013.01); *A61M 39/1011* (2013.01); *A61M 2039/1027* (2013.01); *A61M 2039/1033* (2013.01); *A61M 2039/1066* (2013.01); *A61M 2039/1094* (2013.01); *A61M 2039/267* (2013.01); *A61M 2039/268* (2013.01)
USPC ........................................ 251/149.9; 604/533

(58) Field of Classification Search
USPC ............. 251/149.1, 149, 149.2, 149.4, 149.6, 251/149.8, 149.9, 149.5, 340, 345, 152, 251/223, 216, 218, 344, 343; 604/534, 533, 604/535, 537, 539, 538
See application file for complete search history.

(56) References Cited

U.S. PATENT DOCUMENTS 5,676,346 A * 10/1997 Leinsing .................... 251/149.1
5,806,831 A * 9/1998 Paradis ...................... 251/149.1
(Continued)

FOREIGN PATENT DOCUMENTS

EP          1 747 796 A1     1/2007
WO      WO 02/101269 A1    12/2002
(Continued)

OTHER PUBLICATIONS

International Search Report completed Jun. 22, 2011 and mailed Jun. 23, 2011 from corresponding International Application No. PCT/US2010/047898 filed Sep. 3, 2010 (3 pages).
(Continued)

*Primary Examiner* — John K Fristoe, Jr.
*Assistant Examiner* — Andrew J Rost
(74) *Attorney, Agent, or Firm* — Klein, O'Neill & Singh, LLP

(57) ABSTRACT

The various embodiments include a tubular member having an outlet. A sealing member provides a selective seal over the outlet. When the male connector is connected to a female connector, the tubular member establishes fluid communication between the connectors. In certain embodiments, fluid communication between the connectors may be interrupted even while the connectors are still connected. When the male connector is disconnected from the female connector, the sealing member reestablishes a seal over the outlet.

16 Claims, 21 Drawing Sheets

(56) References Cited

U.S. PATENT DOCUMENTS

| | | | |
|---|---|---|---|
| 6,050,978 A * | 4/2000 | Orr et al. | 604/249 |
| 6,113,068 A * | 9/2000 | Ryan | 251/149.4 |
| 6,364,869 B1 | 4/2002 | Bonaldo | |
| 7,037,302 B2 | 5/2006 | Vaillancourt et al. | |
| 7,118,560 B2 | 10/2006 | Bonaldo | |
| 7,182,313 B2 * | 2/2007 | Doyle | 251/149.6 |
| 7,396,051 B2 * | 7/2008 | Baldwin et al. | 285/354 |
| 2003/0120221 A1 | 6/2003 | Vaillancourt | |
| 2006/0129109 A1 | 6/2006 | Shaw et al. | |
| 2006/0192164 A1 * | 8/2006 | Korogi et al. | 251/149 |
| 2008/0183155 A1 | 7/2008 | Funamura et al. | |
| 2008/0300542 A1 * | 12/2008 | Kitani et al. | 604/131 |

FOREIGN PATENT DOCUMENTS

| | | |
|---|---|---|
| WO | WO 2006/062912 A1 | 6/2006 |
| WO | WO 2006/074935 A1 | 7/2006 |

OTHER PUBLICATIONS

Written Opinion completed Jun. 22, 2011 and mailed Jun. 23, 2011 from corresponding International Application No. PCT/US2010/047898 filed Sep. 3, 2010 (5 pages).

Office Action dated Jul. 29, 2013 from related Chinese Application No. 201080050052.X (6 pages).

English translation of Office Action dated Sep. 22, 2014 from related Chinese Application No. 201080050052.X (5 pages).

Extended European Search Report dated Oct. 7, 2014 from related European Application No. 10814593.9 (8 pages).

* cited by examiner

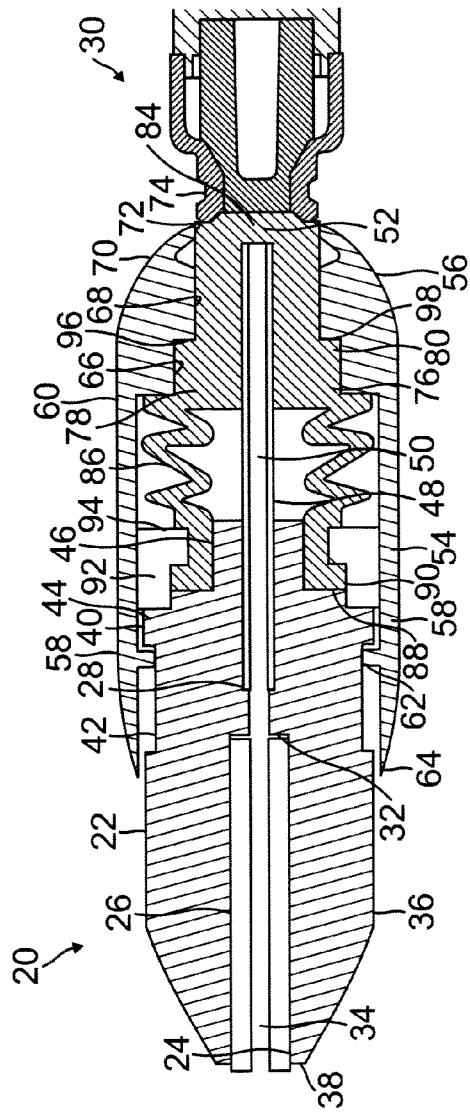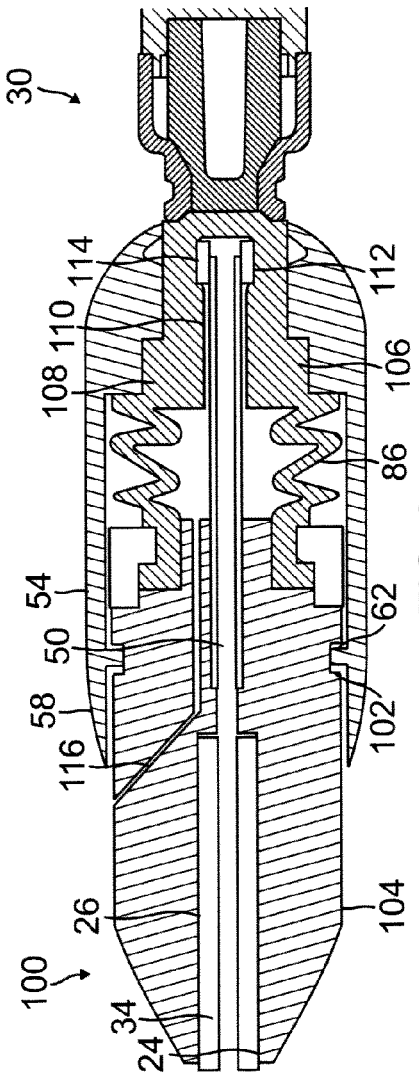

SELECTIVELY SEALABLE MALE NEEDLELESS CONNECTORS AND ASSOCIATED METHODS

CROSS-REFERENCE TO RELATED APPLICATIONS

This is a national phase application under 35 U.S.C. §371 of PCT Application No. PCT/US2010/047898 filed Sep. 3, 2010, which claimed priority to U.S. Provisional application Nos. (1) Ser. No. 61/239,913, filed Sep. 4, 2009; (2) Ser. No. 61/242,281, filed Sep. 14, 2009; and (3) Ser. No. 61/257,338, filed Nov. 2, 2009; the contents of each of which are expressly incorporated herein by reference.

BACKGROUND

The present systems, devices, and methods relate to needleless connectors for transferring fluids.

DESCRIPTION OF RELATED ART

In medical applications, needleless connectors enable fluids to be transferred to a person without the need for repeated needlesticks. For example, a person receiving IV fluids will typically receive the fluids through a catheter. The catheter is operably connected to a needleless connector, sometimes with a short length of IV tubing between the catheter and the connector. Different fluids can be administered to the person through the catheter by connecting different sources of fluids to the needleless connector.

Needleless connectors typically include a male part and a female part. The male part includes an elongate nozzle that engages a complementary receiving opening in the female part. To reduce the likelihood of contamination, the female part may include a seal over its opening. A typical seal is a silicone body having a slit configured to allow the male part to pass to establish fluid communication between the male and female parts. The male part is typically shipped with a removable cover, which is commonly discarded after it is first removed.

SUMMARY

The various embodiments of the present selectively sealable male needleless connector have several features, no single one of which is solely responsible for their desirable attributes. Without limiting the scope of the present embodiments as expressed by the claims that follow, their more prominent features now will be discussed briefly. After considering this discussion, and particularly after reading the section entitled "Detailed Description" one will understand how the features of the present embodiments provide advantages, which include a reduced likelihood of contamination. This advantage is due at least in part to the sealed and swabbable ends of the various embodiments, and, in some embodiments, to the capability of halting flow through the connector without disconnecting it from a female connector.

One embodiment of the present selectively sealable male needleless connector comprises a body defining a first portion of a fluid pathway. The connector further comprises a tubular member extending distally from the body and defining a second portion of the fluid pathway. The tubular member including an outlet at its distal end. The connector further comprises a collar at least partially surrounding the tubular member. The connector further comprises a sealing member at least partially surrounding the tubular member and being, translatable along the tubular member. The connector includes a closed configuration and an open configuration. In the closed configuration the sealing member covers the outlet and in the open configuration the sealing member does not cover the outlet.

Another embodiment of the present application is a method for forming a male needleless connector. The method comprising forming a body defining a first portion of a fluid pathway and forming a tubular member extending in a distal direction away from the first portion and defining a second portion of the fluid pathway that when used with a female needleless connector is closer to the female needleless connector than the first portion. The tubular member includes a fluid opening at its distal end. The method further comprising positioning a collar at least partially surrounding the tubular member and placing a sealing member at least partially surrounding the tubular member and being translatable relative to the tubular member. Wherein the connector includes a closed configuration and an open configuration and in the closed configuration the sealing member covers the fluid opening and in the open configuration the sealing member permits fluid flow through the fluid opening.

A further example of the present application is a method for forming a male needleless connector comprising forming a body comprising a fluid pathway and a tubular member; positioning a seal member around the tubular member so that an opening of the tubular member is sealed by the seal member; and providing a means for venting air from the fluid pathway without removably attaching a vent cap to an open end of the male needleless connector.

A still further example of the present application is a method for connecting a male needleless connector to a female needleless connector comprising engaging a housing opening of the female luer connector into a receiving end of the male needleless connector so that the two connectors are removably engaged to one another; opening a fluid path way of the male needleless connector so that it communicates with the fluid path way of the female needleless connector only after the two connectors are removably engaged. In a specific example, the fluid pathway of the male needleless connector is opened by translating an outer collar relative to a tubular member after the two connectors are removably engaged. In a further example, the fluid pathway of the male needleless connector is vented or purged of air before the outer collar translates.

Embodiments of the present assembly, device, and method further include a male medical connector for use with a female needleless connector, said male medical connector comprising a tubular member comprising a pleated section having at least one side opening.

Embodiments of the present assembly, device, and method further include a male medical connector for use with a female needleless connector, said male medical connector comprising a central flow path and an annular flow path.

Embodiments of the present assembly, device, and method further include a male medical connector for use with a female needleless connector, said male medical connector comprising a tubular member comprising a distal opening, a lateral opening, and an accordion section comprising at least one pleat configured for compressing.

A still further embodiment is a male medical connector assembly comprising a body comprising an inlet and an outlet, means for venting, means for connecting to a female needleless connector, and means for opening a fluid pathway through the body. In a further embodiment, the means for venting does not involve connecting a separately formed vent cap to the outlet or the inlet of the male medical connector assembly.

BRIEF DESCRIPTION OF THE DRAWINGS

The various embodiments of the present selectively sealable male needleless connector now will be discussed in detail with an emphasis on highlighting the advantageous features. These embodiments depict the novel and non-obvious connector shown in the accompanying drawings, which are for illustrative purposes only. These drawings include the following figures, in which like numerals indicate like parts:

FIG. 1 is a side cross-sectional view of one embodiment of the present selectively sealable male needleless connector:

FIG. 2 is a side cross-sectional view of another embodiment of the present selectively sealable male needleless connector;

DETAILED DESCRIPTION

Figure 3:
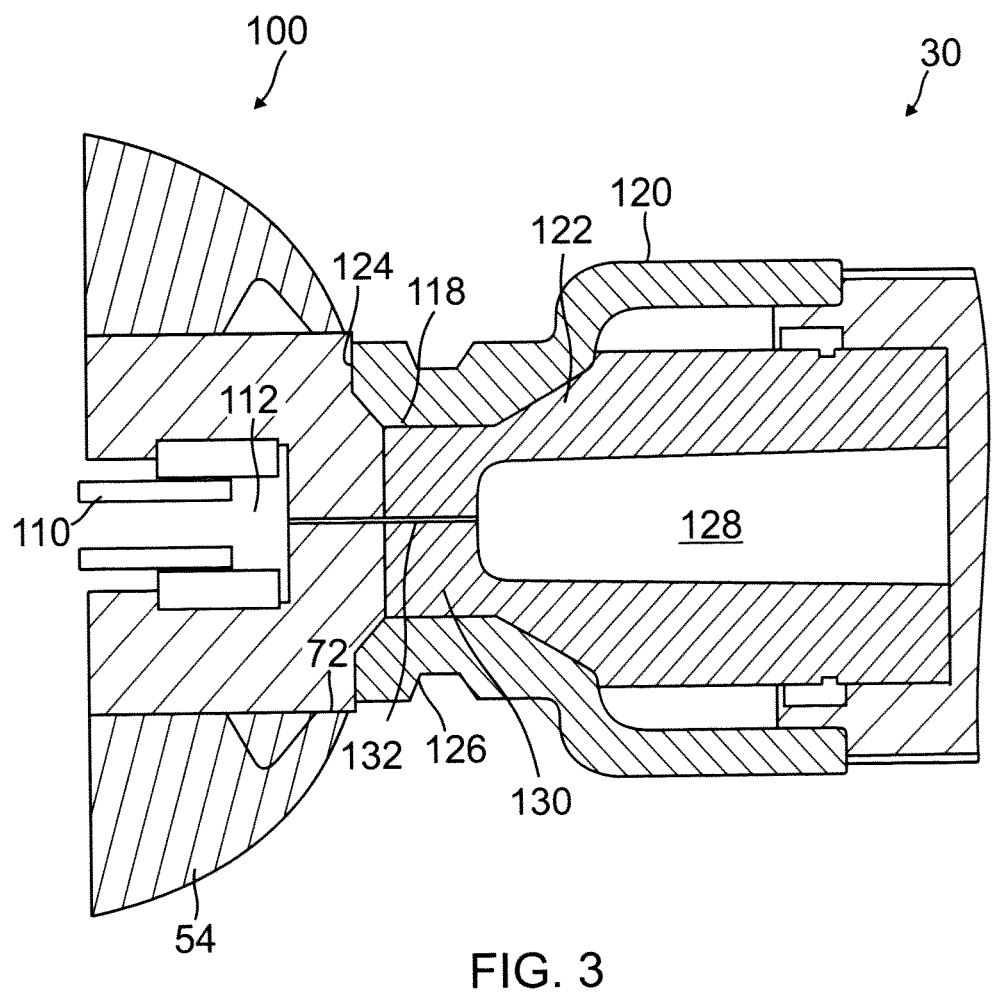
FIG. 3 is a detail view of a selectively sealable male needleless connector similar to that of FIG. 2 abutting a female needleless connector.

The following detailed description describes the present systems, devices, and methods for making and using medical connectors with reference to the drawings. In the drawings, reference numbers label elements of the present embodiments. These reference numbers are reproduced below in connection with the discussion of the corresponding drawing features.

The embodiments of the present selectively sealable male needleless connector are described below with reference to the figures. These figures, and their written descriptions, indicate that certain components of the apparatus are formed integrally, and certain other components are formed as separate pieces. Those of ordinary skill in the art will appreciate that components shown and described herein as being formed integrally may in alternative embodiments be formed as separate pieces. Those of ordinary skill in the art will further appreciate that components shown and described herein as being formed as separate pieces may in alternative embodiments be formed integrally. Further, as used herein the term integral describes a single unitary piece. Within certain context, integral can also mean separately formed components but work together as a single unit.

FIG. 1 illustrates one embodiment of the present selectively sealable male needleless connector 20. The connector 20 is shown in abutting engagement with a female connector 30, which is described in further detail below. The procedure for connecting the male connector 20 to the female connector 30 is also described in further detail below.

The male connector 20 includes a body 22 having a lumen 24 defining a first portion of a fluid pathway. The lumen 24 includes a proximal region 26 and a distal region 28. The proximal region 26 has a larger diameter than the distal region 28. A distal end of the proximal region 26 includes an annular shoulder 32 that marks the transition between the proximal region 26 and the distal region 28. The proximal region 26 is configured to receive intravenous (IV) tubing 34 in a friction fit. Accordingly, the proximal region 26 may include a female taper to facilitate proper insertion and fit for the IV tubing 34.

In the illustrated embodiment, the body 22 is shaped generally as a stepped cylinder. An outer surface 36 of the body 22 tapers inwardly toward the proximal end 38. In an outer distal region 40, the outer surface 36 includes an annular channel 42. Distally of the channel 42, the body 22 steps down to a first smaller diameter 44 and steps down again to a second yet smaller diameter 46.

The body 22 may be formed of any durable material that is also rigid or semi-rigid, such as a plastic. In one embodiment, for example, the body 22 may be formed of polycarbonate.

A tubular member 48 extends distally from the body 22. The tubular member 48 includes a lumen 50 that defines a second portion of the fluid pathway. In the illustrated embodiment, the tubular member 48 is a separate piece received within the distal region 28 of the body lumen 24. A portion of the distal region 28 that receives the tubular member 48 has a diameter substantially equal to an outer diameter of the tubular member 48. A portion of the distal region 28 proximal to the portion that receives the tubular member 48 has a diameter substantially equal to an inner diameter of the tubular member 48. At its distal end, the tubular member 48 defines an outlet 52 of the fluid pathway 24, 50. In one embodiment, the tubular member 48 is made from a thermoplastic material and is co-molded with the body 22. However, those of ordinary skill in the art will appreciate that in alternative embodiments the body 22 and the tubular member 48 may be formed as a single unitary piece and/or made from different materials, such as metals.

The connector 20 further comprises a collar 54 that at least partially surrounds the tubular member 48. In the illustrated embodiment, the collar 54 includes a distal portion 56 that is shaped substantially as a tapered cylinder. Cantilevered wings 58, shaped like extended tabs in one embodiment, extend proximally from a proximal outer edge 60 of the distal portion 56 and engage the body 22. In the illustrated embodiment, two wings 58 are shown diametrically opposed from one another. In alternative embodiments, additional wings 58 may be provided, or the wings 58 may be replaced by a cylindrical proximal extension from the proximal outer edge 60 of the distal portion 56.

An inner surface of each wing 58 includes a protruding boss 62 spaced from a proximal end 64 of each wing 58. In the illustrated embodiment, each boss 62 has a substantially rectangular cross-section. However, those of ordinary skill in the art will appreciate that the bosses 62 may have any shape. The bosses 62 seat within the annular channel 42 in the body 22. A width of the channel 42 is greater than a width of each boss 62. The collar 54 is thus translatable along the body 22 between the limits defined by the ends of the channel 42, as discussed in further detail below. The collar 54 is also rotatable about the body 22 to facilitate mating with the female needleless connector 30, as also discussed in further detail below.

In the distal portion 56, an outer diameter of the collar 54 tapers inwardly. Also in the distal portion 56, an inner diameter of the collar 54 steps down to a first smaller diameter 66 and steps down again to a second yet smaller diameter 68. Distally of the second smaller diameter region 68, the interior diameter of the collar 54 increases and then decreases again to the distal end 70. The distal end 70 includes internal threads 72 that enable the collar 54 to securely engage external threads 74 on the female needleless connector 30 by rotating the collar relative to the connector, as discussed in further detail below.

The collar 54 may be formed of any durable material that is also rigid or semi-rigid, such as a plastic. In one embodiment, for example, the collar 54 may be formed of polypropylene.

The connector 20 further comprises a sealing member 76. The sealing member 76 may be formed of any pliable and resilient material that is capable of forming a seal when abutting the material of the tubular member 48. The sealing member 76 material is also preferably capable of forming a seal when abutting itself. For example, if a mass of the sealing member material includes a slit 84, the abutting sidewalls of the slit 84 preferably form a seal that blocks liquid penetration into the slit 84 until the walls of the slit 84 are manually separated. In one embodiment, for example, the sealing member 76 may be formed of silicone. In other embodiments, various thermoplastic elastomers (TPEs) may be used to form the sealing member 76. The sealing member may also be impregnated and/or coated with antimicrobial agents. In one embodiment, antimicrobial compositions are provided for controlling or combating bacterial contamination inside a valve, such as reducing the amount of biofilm formation. Use of antimicrobial compositions in medical devices is well known in the art and is described in, for example, U.S. Pat. No. 4,603,152 to Laurin et al., U.S. Pat. No. 5,049,139 to Gilchrist, and U.S. Pat. No. 5,782,808 to Folden. Use of antimicrobial compositions is also disclosed in U.S. Patent Application Publication Nos. 2002/0133124 A1 and 2003/0199835 A1, both to Leinsing et al. The contents of these patents and publications are incorporated herein by reference as if set forth in full.

The sealing member 76 includes a distal region 78 that partially surrounds and snugly engages the tubular member 48. The distal region 78 is shaped as a stepped cylinder. A first larger diameter portion 80 of the distal region 78 seats within the first smaller diameter portion 66 of the collar 54. A second smaller diameter portion 82 of the distal region 78, located distally of the first portion 80, seats within the second smaller diameter portion 68 of the collar 54. The second portion 82 of the sealing member 76 extends around the outlet 52 of the tubular member 48, sealing the outlet 52. The second portion 82, however, includes a slit 84 located distally of the outlet 52. The slit 84 is sealed in the closed configuration of FIG. 1. However, the sidewalls of the slit 84 may be manually separated as described below to enable fluid to flow out of the outlet 52.

A cylindrical skirt section 86 extends proximally from a proximal outer edge of the first portion 80 of the sealing member distal region 78. A proximal end 88 of the skirt 86 includes an outwardly extending annular flange 90 on its outer surface. In an unconstrained state, the skirt 86 would be shaped substantially as a smooth cylinder. However, in the configuration shown in FIG. 1 the skirt 86 is deformed as a result of being compressed between the collar distal portion 56 and the body 22. Stored energy in the skirt 86 biases both the sealing member 76 and the collar 54 toward the outlet 52 of the tubular member 48. Thus, when the connector 20 is at rest the sealing member 76 covers and seals the outlet 52. The sealing member 76 is, however, translatable proximally along the tubular member 48, as described in further detail below. In an alternative embodiment, the skirt 86 may be replaced by a plurality of legs. To facilitate biasing the collar and/or the sealing member toward the outlet 52, a helical coil spring may also be used and mounted coaxially with the tubular member 48.

The connector 20 further comprises an annular ring 92. A proximal end of the ring 92 seats about the first smaller diameter distal region 44 of the body 22. The remainder of the ring 92 surrounds, but is spaced from, the second smaller diameter distal region 46 of the body 22. The proximal end 88 of the skirt 86 on the sealing member 76 occupies the space between the ring 92 and the second smaller diameter distal region 46. The ring 92 includes an annular flange 94 around its inner surface at its distal end. The flange 94 forms a barrier for the annular flange 90 on the skirt 86, preventing the proximal end of the skirt 86 from escaping the space between the ring 92 and the body 22.

In use, the connector 20 receives IV tubing 34 in the proximal region 26 of its lumen 24. The IV tubing 34 carries liquid, such as saline, for introduction into a person's vasculature. When the IV tubing 34 is first inserted into the proximal region 26 of the lumen 24, air may be trapped in the fluid passageway 24, 50 distally of the liquid in the IV tubing 34. It is desirable to clear this air from the connector 20 prior to introducing the IV liquid into the person's vasculature. Thus, the connector 20 of FIG. 1 includes a priming feature.

To prime the connector 20, the operator pulls the collar 54 proximally with respect to the body 22. As the collar 54 moves proximally along the body 22, it pulls the sealing member 76 proximally over the tubular member 48 as the annular shoulder 96 on the collar 54 bears against the annular shoulder 98 on the sealing member 76. As the sealing member 76 moves proximally over the tubular member 48, the outlet 52 of the tubular member 48 forces its way through the slit 84 until the outlet 52 extends distally of the slit 84. In that configuration, the outlet 52 is no longer sealed and the IV liquid may flow freely through the fluid pathway and out the outlet 52. The operator may need to hold the connector 20 at an elevation below the source of the IV liquid (which may be, for example, a standard IV bag) in order to start the flow through the connector 20.

The liquid flowing 58 through the fluid pathway 24, 50 forces any air in the pathway out the outlet 52. Thus, when the operator sees that liquid is beginning to flow out the outlet 52, he or she knows that the connector 20 has been primed. He or she then releases the collar 54, allowing it to move distally under the influence of the biasing sealing member 76. As the sealing member 76 moves distally it wraps around the outlet 52 of the tubular member 48, resealing the outlet 52. The fluid pathway 24, 50 is now filled with liquid, and the connector 20 can be used to introduce the IV liquid into the person's vasculature. The process for using the connector 20 to introduce IV liquid into a person's vasculature is described below with respect to FIGS. 2-4.

FIG. 2 illustrates another embodiment of the present selectively sealable male needleless connector 100. The connector 100 is similar to the embodiment described above and illustrated in FIG. 1. However, in the connector 100 of FIG. 2, the annular channel 102 in the body 104 is narrower. In fact, the channel 102 has approximately the same width as each of the bosses 62 on the wings 58. The collar 54 is thus translatable with respect to the body 104 only a small distance, or not at all. The collar 54 is, however, rotatable with respect to the body 104 to facilitate threaded engagement with the female connector 30.

The distal region 106 of the sealing member 108 is spaced from the tubular member 110, both along the length of the tubular member 110 and at the outlet 112. The connector 100 of FIG. 2 further comprises a porous membrane 114, also known as a hydrophobic filter, encircling the outlet 112. The porous membrane 114 is shaped as a short cylinder, and closely engages the tubular member 110 on its outer surface and the sealing member 108 on its inner surface. The porous membrane 114 includes a plurality of very fine perforations (not shown) that are configured to allow gaseous particles to pass through the membrane 114 and to block liquid particles from passing through the membrane 114. The membrane 114 thus provides a flow path for air, enabling the connector 100 to be primed as described below. The porous membrane 114 can be made from any of a number of suitable materials well known to those skilled in the art, such as super hydrophobic polyvinyldiflouride (PVDF).

With further reference to FIG. 2, the body 104 includes a vent 116 that facilitates priming the connector 100. The vent 116 comprises a passageway that extends through a distal portion of the body 104 substantially parallel to a longitudinal axis of the body 104. The vent 116 then bends at approximately 45° and extends diagonally before terminating at the outer surface of the body 104 proximally of the collar 54. The vent 116 provides an escape path for air that is forced out of the lumens 24, 50 during priming, as described below.

To prime the connector 100 of FIG. 2, the operator connects IV tubing 34 to the proximal region 26 of the body lumen 24. The operator then holds the connector 100 at an elevation beneath the source of IV liquid (such as an IV bag). The liquid flows into the lumens 24, 50, forcing the air distally through the outlet 112 and through the porous membrane 114. The air then travels proximally along the outside of the tubular member 110, into the space inside the skirt 86, then through the vent 116 and finally to the ambient atmosphere. The vent 116 thus facilitates priming by enabling fluid pressure within the connector 100 to stabilize with the ambient pressure. The connector 100 of FIG. 2 can thus be primed without the need to translate the collar 54 along the body 104 and expose the outlet 112 of the tubular member 110 to the ambient atmosphere. Thus, an aspect of the present embodiments is a connector capable of being primed without the use of a venting cap.

Figure 4:
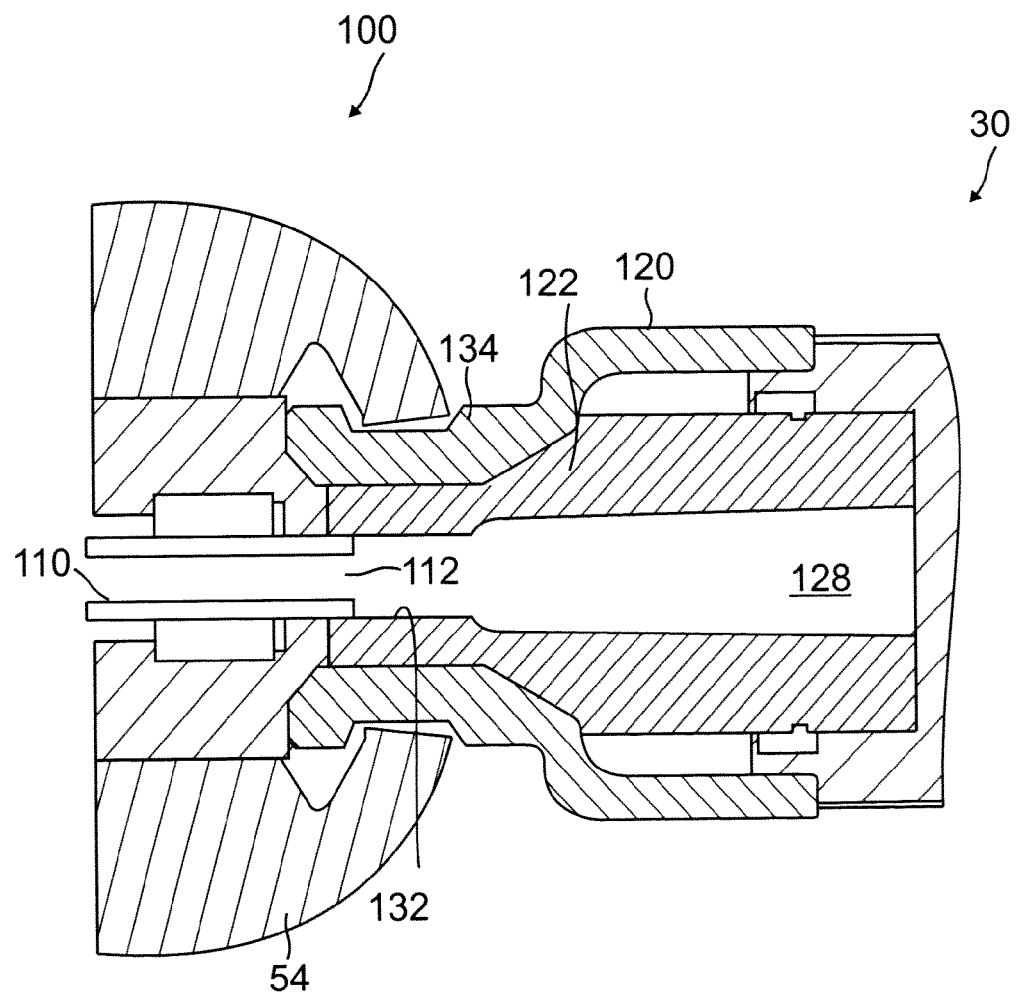
FIG. 4 is a detail view of the selectively sealable male needleless connector of FIG. 3 connected to the female needleless connector of FIG. 3.

FIGS. 3 and 4 illustrate steps in connecting a connector 100 similar to that of FIG. 2 to a female connector 30. The steps of securing the connectors 30, 100 to one another are described below. The steps are somewhat similar when using the connector 20 of FIG. 1 except for the priming aspect.

The operator begins by priming the male connector 100 according to the process described above with respect to FIG. 2. The operator then positions the male connector 100 so that a distal face 118 of the sealing member 108 abuts the female connector 30, as shown in FIG. 3. The illustrated female connector 30, which is merely one example, includes a rigid housing 120 containing a pliable and resilient sealing member 122. A proximal end of the housing 120 comprises a generally cylindrical inlet port 124 having external threads 126. The sealing member 122 includes a lumen 128 that does not extend completely to the proximal end 124 of the housing 120. Instead, an end wall 130 of the sealing member 122 closes the proximal end of the lumen 128. However, the end wall 130 includes a transverse slit 132 that opens fluid communication to the lumen 128 when the sealing member 122 is deformed, as described below.

With continued reference to FIG. 3, with the male and female connectors 30, 100 abutting one another, the operator next applies digital pressure to urge the connectors 30, 100 closer to one another. The rigid housing 120 of the female connector 30 pushes the sealing member 108 proximally with respect to the collar 54 and the female connector 30 advances into the distal end of the collar 54. The operator continues urging the connectors 30, 100 closer to one another until the threads 72 on the male connector 100 engage the threads 126 on the female connector 30. At that point the operator twists the collar 54 while holding the female connector 30 steady so that the engaged threads 72, 126 cause the female connector 30 to advance farther into the collar 54. Advantageously, the collar 54 is rotatable about the body 104 so that IV tubing attached to either connector 30, 100 does not get twisted as the operator rotates the collar 54.

With continued reference to FIG. 3, as the female connector 30 advances into the collar 54, the rigid housing 120 pushes the sealing member 108 in the male connector 100 proximally along the tubular member 110. The sealing member 108 deforms, opening up the slit 84. The outlet 112 of the tubular member 110 eventually forces its way through the slit 84. As the female connector 30 advances into the collar 54, the sealing member 108 in the male connector 100 and the sealing member 122 in the female connector 30 push against one another. The sealing member 122 in the female connector 30 also deforms, opening up the slit 132 in the sealing member 122. The outlet 112 of the tubular member 110 eventually forces its way through the slit 132 in the female connector sealing member 122, opening fluid communication between the connectors 30, 100, as shown in FIG. 4. The female connector 30 stops advancing into the male connector 100 when the distal end of the collar 54 contacts a proximally facing annular shoulder 134 on the female connector 30.

To disengage the connectors 30, 100, the operator rotates the collar 54 in the opposite direction with respect to the female connector 30. As the collar 54 rotates, the engaged threads 72, 126 cause the female connector 30 to withdraw from the male connector 100. As the female connector 30 withdraws, the sealing members 108, 122 return to their original shapes, resealing both connectors 30, 100. When the threads 72, 126 have completely disengaged, the operator pulls the connectors 30, 100 apart.

Those of ordinary skill in the art will appreciate that the steps described above for engaging the male connector 100 with a female connector 30 may also apply to other embodiments of the present male connector. Generally, however, the above method applies to any of the connectors in which the collar is either not translatable with respect to the body (as in the embodiment of FIG. 2), or in which the connector is intended to be connected to a female connector 30 when the collar is disposed at its extreme distal position with respect to the body (as in the embodiment of FIG. 1).

FIGS. 5-10 illustrate additional embodiments of the present selectively sealable male needleless connector. Each of these connectors is configured to occlude fluid communication between the male connector and a female connector, even while the male connector remains connected to the female connector.

Figure 5:
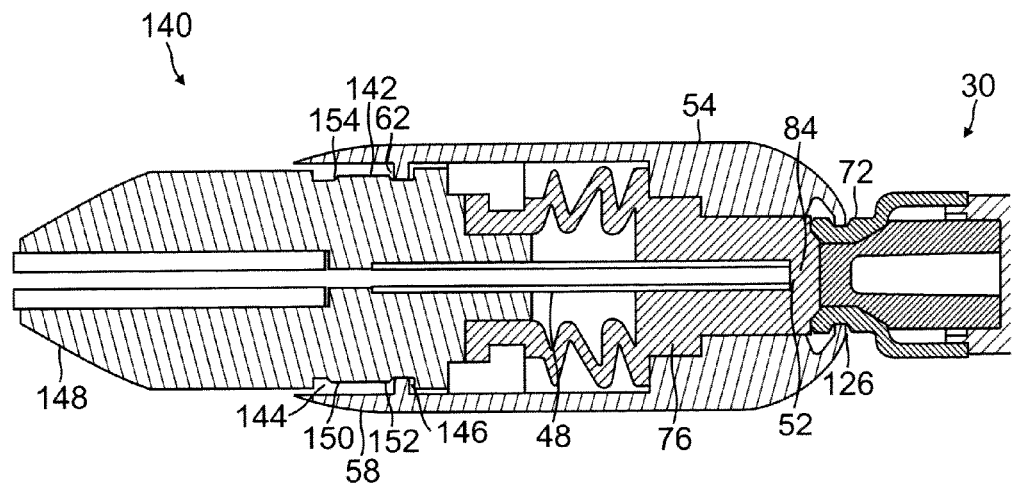
FIG. 5 is a side cross-sectional view of another embodiment of the present selectively sealable male needleless connector and a female needleless connector.

The connector 140 of FIG. 5 is similar to the embodiment described above and illustrated in FIG. 1. However, in the connector 140 of FIG. 5 the annular channel 142 in the body 148 includes a variable depth. At either end 144, 146, the channel 142 has a greater depth than at locations intermediate the two ends 144, 146. A diameter of the channel 142 in the shallower intermediate locations is greater than an inner diameter measured between the bosses 62 on the collar 54. A diameter of the channel 142 at either of the deeper ends 144, 146 is approximately equal to the inner diameter measured between the bosses 62 on the collar 54. Thus, when the bosses 62 are disposed in either of the deeper ends 144, 146, to translate the collar 54 along the body 148 the wings 58 flex outward to enable the protruding bosses 62 to ride up onto the shallower intermediate portion 150 of the channel 142. Either end of the shallower intermediate portion may include a ramped surface 152 to facilitate the bosses 62 riding up onto the shallower intermediate portion 150. When the bosses 62 reach the deeper channel end 144, 146 on the opposite side, stored energy in the wings 58 causes them to contract radially. The operator experiences a tactile sensation and hears an audible click as the bosses 62 snap inward into the deeper channel ends 144, 146.

The relative dimensions of the bosses 62 and the deeper proximal end 144 of the channel 142, as well as other structural characteristics of the body 148 and collar 54, may be configured to enable the collar 54 to remain at its proximal limit along the body 148 even when the operator is not restraining the collar 54. For example, the shallow portion 150 of the channel 142 may include a proximal lip 154 that is oriented at a sufficient angle to bear against the distal surfaces of the bosses 62 to retain the bosses 62 against the biasing force of the sealing member 76.

Figure 6:
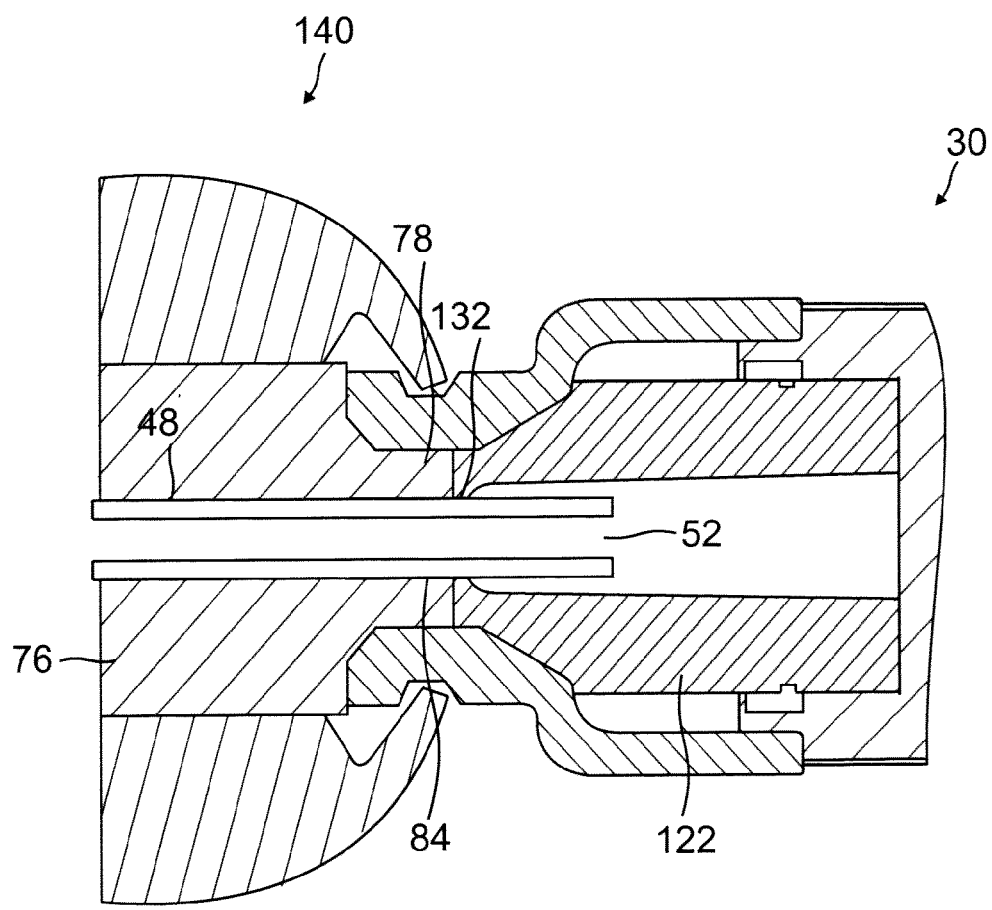
FIG. 6 is a detail view of the selectively sealable male needleless connector and the female needleless connector of FIG. 5, illustrating the connectors open for fluid communication.

To connect the male connector 140 of FIG. 5 to a female connector 30, the operator engages the internal threads 72 on the distal end of the collar 54 with the external threads 126 on the female connector 30, as shown in FIG. 5. In this configuration the sealing member 76 covers the outlet 52 of the tubular member 48. There is thus no fluid communication between the connectors 30, 140. To open fluid communication, the operator may advance the tubular member 48 through the slit 84 in the sealing member 76 by pulling the collar 54 proximally along the body 148. As the collar 54 advances proximally along the body 148, the tubular member 48 advances distally through the slit 84 in the sealing member 76. The advancing tubular member 48 forces the distal end 78 of the sealing member 76 to deform and move distally into the female connector 30, as shown in FIG. 6. The sealing member 76 of the male connector 140 in turn deforms the sealing member 122 of the female connector 30, opening the slit 132 in the sealing member 122. The tubular member 48 continues advancing until it extends through both slits 84, 132 in both sealing members 76, 122, as shown in FIG. 6. In this configuration, fluid communication is open between the male connector 140 and the female connector 30.

With the male connector 140 of FIG. 5, the operator may advantageously reseal the outlet 52 of the tubular member 48 without disconnecting the male connector 140 from the female connector 30. To do so, he or she advances the collar 54 distally along the body 148. When the bosses 62 reach the distal end 146 of the annular channel 142, the sealing member 76 completely covers the outlet 52 of the tubular member 48 and the tubular member 48 is resealed, as shown in FIG. 5. Resealing the tubular member 48 without disconnecting the connectors 30, 140 is advantageous, because it reduces the likelihood of contamination. When connectors are disconnected, their ends are exposed and can become contaminated by contact with other surfaces or by attracting airborne contaminants. With the male connector 140 of FIG. 5, the ends of the connectors 30, 140 remain in abutting engagement even when the tubular member 48 is backed out of the female connector 30. The abutting surfaces of the connectors 30, 140 resist penetration of contaminants, reducing the likelihood that the liquid path through the connectors 30, 140 will become contaminated. Thus, one aspect of the present embodiments is a male connector comprising an axially movable collar, the collar comprising an inside thread for engaging a female connector, and the collar being structured to move both a seal member positioned inwardly of the collar and the female connector axially to at least one of opening the female connector and closing the female connector without separating the movable collar from the female connector.

Figure 7:
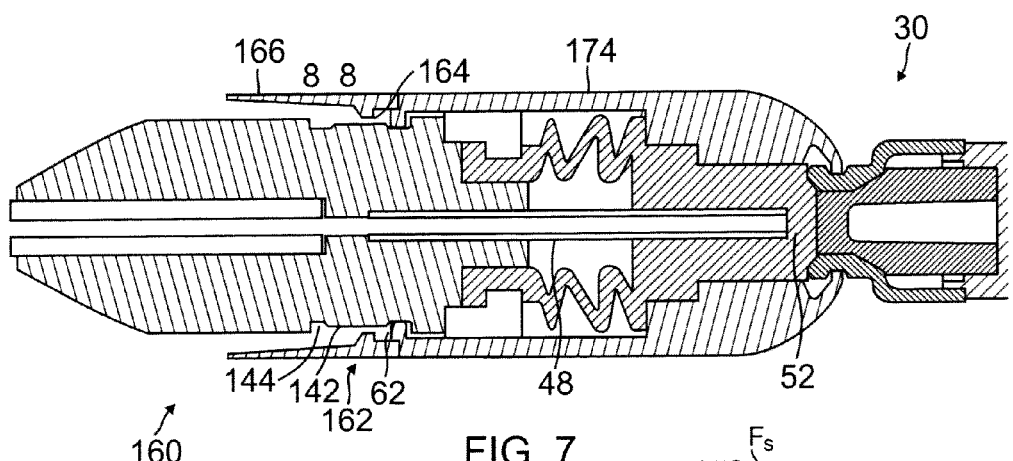
FIG. 7 is a side cross-sectional view of another embodiment of the present selectively sealable male needleless connector and a female needleless connector.
Figure 8:
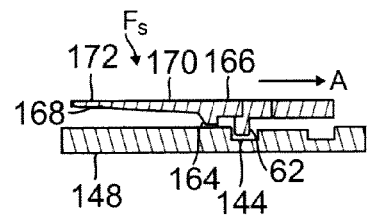
FIG. 8 is a detail view of the clutch feature of the selectively sealable male needleless connector of FIG. 7, indicated by the circle 8-8 in FIG. 7.

FIG. 7 illustrates another embodiment of the present selectively sealable male needleless connector 160. The connector 160 is similar to the embodiment described above and illustrated in FIG. 5. For example, the male connector 160 of FIG. 7 also enables the outlet 52 of the tubular member 48 to be resealed without disconnecting the male connector 160 from the female connector 30. However, the connector 160 of FIG. 7 further includes a clutch mechanism 162 that assists the operator in disengaging the bosses 62 from the deeper proximal end 144 of the channel 142. FIG. 8 shows a detail view of the clutch mechanism 162.

With reference to FIG. 7, the clutch mechanism 162 includes second bosses 164 on the inner surfaces of the wings 166. The second bosses 164 are positioned proximally of the first bosses 62. The second bosses 164 further have a lesser height than the first bosses 62. An inner diameter measured between the second bosses 164 is approximately equal to an outer diameter of the body 148 in the region just proximal to the annular channel 142. The second bosses 164 can thus ride freely over the body 148 as the operator pulls the collar proximally over the body 148.

With reference to FIG. 8, the clutch mechanism 162 further includes a taper on the inner surfaces 168 of the proximal portions of the wings 166. However, the outer surfaces 170 of the proximal portions do not taper. The tapered inner surfaces cause the wall thickness of the wings 166 to decrease from the location of the second bosses 164 to the proximal ends 172 of the wings 166. The proximal ends 172 of the wings 166 are thus spaced a greater distance from the body 148 than portions of the wings 166 located distally of the proximal ends 172. The spacing enables the operator to provide digital squeezing pressure at the proximal ends 172. The arrow $F_S$ in FIG. 8 indicates the location and direction of the applied squeezing pressure. Under the influence of the squeezing pressure, the portion of each wing 166 proximal the second boss 164 acts as a lever, with the second boss 164 acting as a fulcrum. Portions of the wings 166 located distally of the second bosses 164, in the area of the first bosses 62, expand as the squeezing pressure is applied at the proximal ends 172. The expansion causes the first bosses 62 to rise up out of the deep proximal end 144 of the annular channel 142. As the first bosses 62 exit the deep proximal end 144, they no longer restrain translation of the collar 174 relative to the body 148 and the collar 174 may slide distally along the body 148 under the influence of the biasing sealing member, as indicated by the arrow A in FIG. 8.

Figure 9:
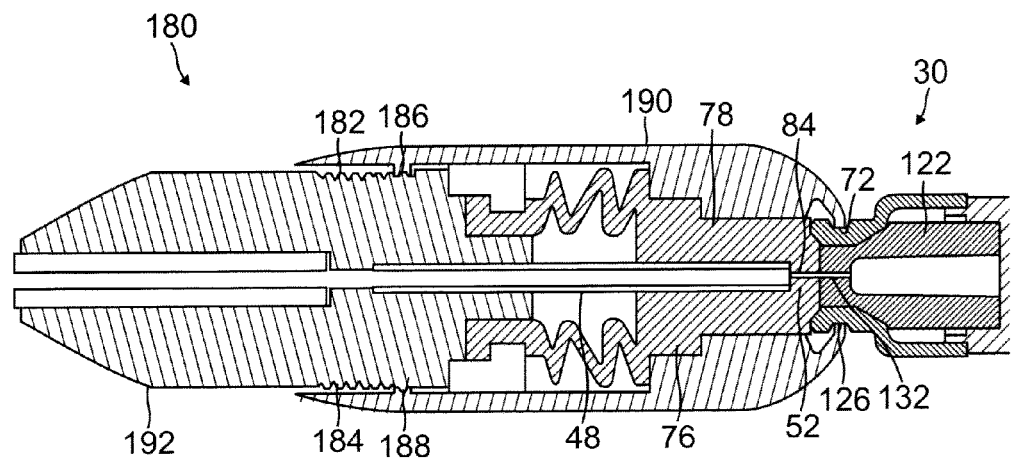
FIG. 9 is a side cross-sectional view of another embodiment of the present selectively sealable male needleless connector and a female needleless connector.

FIG. 9 illustrates another embodiment of the present selectively sealable male needleless connector 180. The connector 180 is similar to the embodiment described above and illustrated in FIG. 5. However, in the connector 180 of FIG. 9 the channel 182 includes a constant depth and external threads 184. The bosses 186 further include internal threads 188. Relative rotation of the collar 190 and the body 192 thus induces translational movement of the collar 190 along the body 192.

To connect the male connector 180 of FIG. 9 to a female connector 30, the operator engages the internal threads 72 on the distal end of the collar 190 with the external threads 126 on the female connector 30, as shown in FIG. 9. In this configuration the sealing member 76 covers the outlet 52 of the tubular member 48. There is thus no fluid communication between the connectors 30, 180. To open fluid communication, the operator may advance the tubular member 48 through the slits 84, 132 in the sealing members 76, 122 by rotating the body 192 relative to the collar 190 while maintaining the angular alignment of the collar 190 and the female connector 30.

The relative rotation of the body 192 and the collar 190 advances the body 192 proximally into the collar 190, which in turn advances the tubular member 48 through the slit 84 in the sealing member 76. The advancing tubular member 48 forces the distal end 78 of the sealing member 76 to deform and move distally into the female connector 30. The sealing member 76 of the male connector 180 in turn deforms the sealing member 122 of the female connector 30, opening the slit 132 in the sealing member 122. The tubular member 48 continues advancing until it extends through both slits 84, 122 in both sealing members 76, 122. In this configuration, fluid communication is open between the male connector 180 and the female connector 30.

With the male connector 180 of FIG. 9, the operator may advantageously reseal the outlet 52 of the tubular member 48 without disconnecting the male connector 180 from the female connector 30. To do so, he or she rotates the body 192 relative to the collar 190 in the opposite direction from that used to advance the body 192 farther into the collar 190. Engagement of the threads 184, 188 causes the body 192 to back out of the collar 190. When the bosses 186 reach the distal end of the annular channel 182, as in FIG. 9, the sealing member 76 completely covers the outlet 52 of the tubular member 48 and the tubular member 48 is resealed.

Figure 10:
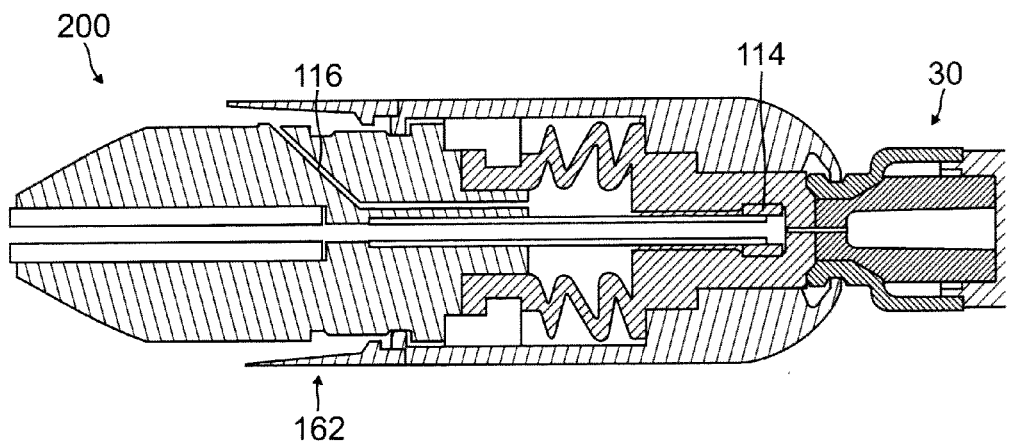
FIG. 10 is a side cross-sectional view of another embodiment of the present selectively sealable male needleless connector and a female needleless connector.

FIG. 10 illustrates another embodiment of the present selectively sealable male needleless connector 200. The connector 200 combines features of the embodiments described above and illustrated in FIGS. 2 and 7. For example, the connector 200 includes the porous membrane 114 and the vent 116 of FIG. 2, which together facilitate priming. The connector 200 further includes the clutch mechanism 162 of FIG. 7.

Figure 11:
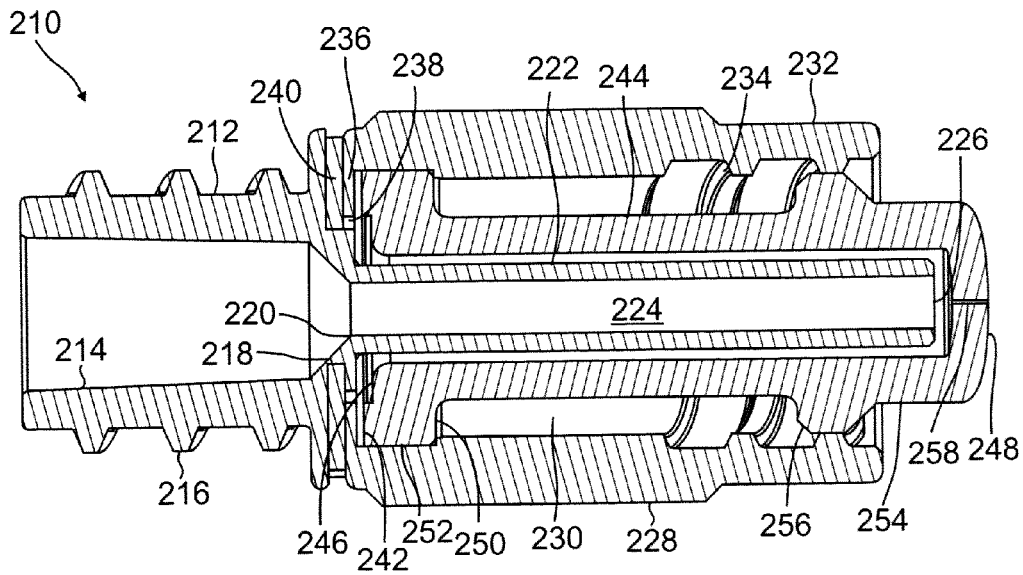
FIG. 11 is a side cross-sectional view of another embodiment of the present selectively sealable male needleless connector.

FIG. 11 illustrates another embodiment of the present selectively sealable male needleless connector 210. The connector 210 includes a body 212 that is shaped substantially as a hollow cylinder. The body 212 includes a lumen 214 defining a first portion of a fluid pathway. The lumen 214 includes a female taper. The lumen 214 is thus configured to receive intravenous (IV) tubing (not shown) in a friction fit. An outer surface of the body 212 includes threads 216 to accommodate a male Luer or a male threaded Luer, which has a threaded collar.

In a distal region, the taper of the lumen 214 increases sharply, creating a tapered shoulder 218 that continues to a distal end 220 of the lumen 214. A tubular member 222 extends distally from the body 212. The tubular member 222 also includes a lumen 224 that defines a second portion of the fluid pathway. At its distal end, the tubular member 222 defines an outlet 226 of the fluid pathway 214, 224. In the illustrated embodiment, the tubular member 222 is formed integrally as a single piece with the body 212. However, those of ordinary skill in the art will appreciate that in alternative embodiments the body 212 and the tubular member 222 could be formed as separate pieces.

The connector 210 further comprises a collar 228 that extends distally from the body 212 and at least partially surrounds the tubular member 222. In one embodiment, the body 212 and the collar 228 are formed as separate pieces that are secured together. The body 212 and the collar 228 could, for example, be welded or adhered to one another. Those of ordinary skill in the art will appreciate that in alternative embodiments the body 212 and the collar 228 may formed integrally as a single piece.

In the illustrated embodiment, the collar 228 is shaped substantially as a cylinder. An annular space 230 separates the collar 228 from the tubular member 222. A distal region 232 of the collar 228 includes threads 234 on its internal surface. The threads 234 are configured to mate with external threads on a female connector (not shown), as described in detail below.

A proximal end wall 236 of the collar 228 includes at least one aperture 238. In the illustrated embodiment, two apertures 238 are shown diametrically opposed from one another. Those of ordinary skill in the art will appreciate that any number of apertures 238 may be provided. The apertures 238 extend completely through the collar's proximal end wall 236 at locations spaced from the tubular member 222. A proximal end of each aperture 238 is in fluid communication with a passageway 240 that extends substantially perpendicularly to a longitudinal axis of the connector 210. The passageways 240 may be formed in the body 212, or in the collar 228, or in a combination of both. Together each aperture 238 and passageway 240 forms a vent that facilitates priming the connector 210, as described in detail below.

As in the previous embodiments, the body 212 and the collar 228 may be formed of any durable and rigid or semi-rigid materials, such as plastics. In one embodiment, for example, the body 212 and/or the collar 228 may be formed of polycarbonate or polypropylene.

A porous membrane 242 abuts a distal surface of the collar's proximal end wall 236. In the illustrated embodiment, the porous membrane 242 is shaped as a ring having an internal diameter that is substantially equal to an external diameter of the tubular member 222 and an external diameter that is substantially equal to an internal diameter of the collar 228 at its proximal end. The porous membrane 242 thus covers the distal ends of the apertures 238. As in the previous embodiments, the porous membrane 242 includes a plurality of very fine perforations that are configured to allow gaseous particles to pass through the membrane 242 and to block liquid particles from passing through the membrane 242. The membrane 242 thus provides a flow path for air, enabling the connector 210 to be primed as described below. The porous membrane 242 can be made from any of a number of suitable materials well known to those skilled in the art, such as super hydrophobic polyvinyldifluoride (PVDF).

The annular space 230 between the collar 228 and the tubular member 222 receives a sealing member 244. As in the previous embodiments, the sealing member 244 may be formed of any pliable and resilient material that is capable of forming a seal when abutting itself. In one embodiment, for example, the sealing member 244 may be formed of silicone.

The sealing member 244 is shaped substantially as a hollow cylinder that is open at its proximal end 246 and closed at its distal end 248. The proximal end 246 of the sealing member 244 includes an outwardly extending flange 250. The flange 250 seats within an annular recess 252 in the inner surface of the collar 228 adjacent its proximal end wall 236. Engagement of the flange 250 and the recess 252 assists in maintaining the position of the proximal end 246 of the sealing member 244 within the annular space 230. A distal region 254 of the sealing member 244 includes an outwardly extending flange 256 at a location spaced proximally from the distal end 248 of the sealing member 244. The flange 256 reinforces the distal region 254 of the sealing member 244 to reduce the likelihood that the slit 258 will crack under fluid pressure inside the connector 210. The flange 256 thus assists in reducing the likelihood of leaking when the connector 210 is not connected to a female connector.

The sealing member 244 at least partially surrounds the tubular member 222, including the outlet 226. However, the sealing member 244 is spaced from the tubular member 222 along its length and at the outlet 226. The distal end wall 248 of the sealing member 244 includes a slit 258. The slit 258 is sealed in the closed configuration of FIG. 11. However, the sidewalls of the slit 258 may be manually separated as described below to enable fluid to flow out of the outlet 226 and into a female connector.

In use, the connector 210 receives IV tubing (not shown) in the body lumen 214. To prime the connector 210, the operator first connects IV tubing of the connector 210 to a source of IV liquid. The operator then holds the connector 210 at an elevation beneath the source of IV liquid (such as an IV bag). The liquid flows into the lumens 214, 224, forcing the air distally through the lumens 214, 224 and out the outlet 226 of the tubular member 222. The air then travels proximally along the outside of the tubular member 222, through the porous membrane 242, through the vents 238, 240 and finally to the ambient atmosphere. The vents 238, 240 thus facilitate priming.

To connect the male connector 210 of FIG. 11 to a female connector, an operator positions the distal end wall 248 of the sealing member 244 in contact with the proximal end of the female connector. While FIG. 11 does not illustrate a female connector, the female connector may be similar in structure to the female connectors illustrated in the foregoing figures. The distal end wall 248 of the sealing member 244 bears against a proximal face of a sealing member in the female connector. The distal end wall 248 also bears against a proximal rim of a rigid housing of the female connector. The housing includes external threads configured to mate with the internal threads in the distal region of the collar 228.

To engage the threads, the operator applies digital pressure to advance the collar 228 on the male connector 210 toward the rigid housing on the female connector. As the two components move closer together, the rigid housing of the female connector forces the sealing member 244 proximally along the tubular member 222. As the sealing member 244 is pushed back, the outlet 226 of the tubular member 222 pushes its way through the slit 258 in the sealing member 244. At the same time, the distal region 254 of the sealing member 244 deforms as it bears against the proximal face of the sealing member in the female connector. The female connector's sealing member deforms and collapses into the housing, opening a slit in the female connector's sealing member. To complete the connection, the operator twists the male connector 210 relative to the female connector once the threads are engaged. When the two connectors are screwed together completely, fluid communication is open between the connectors, with the tubular member 222 extending through the slits in both sealing members.

Figure 12:
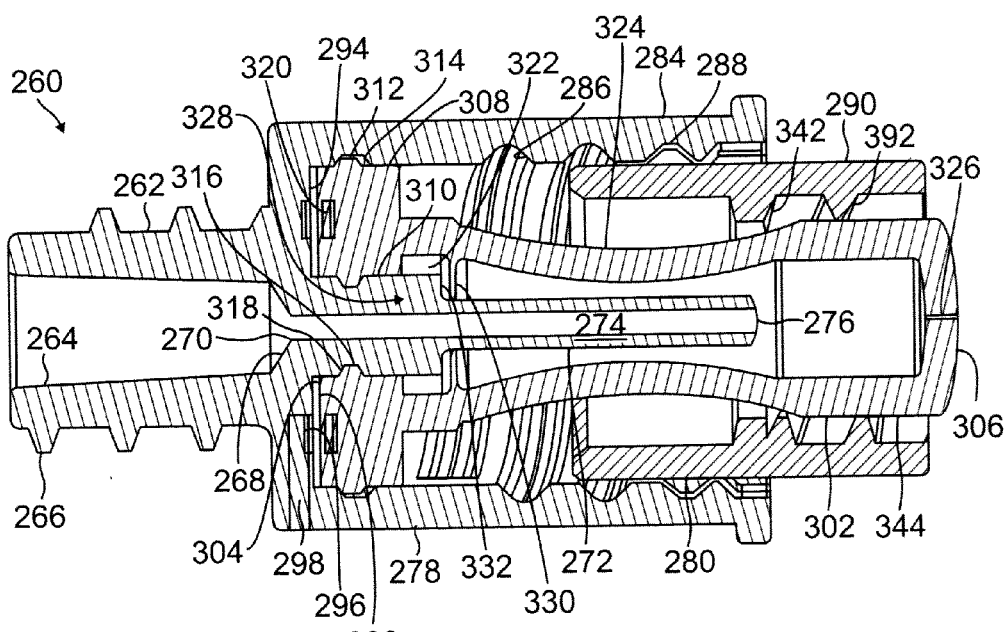
FIG. 12 is a side cross-sectional view of another embodiment of the present selectively sealable male needleless connector.

FIG. 12 illustrates another embodiment of the present selectively sealable male needleless connector 260. The connector 260 includes a body 262 that is shaped substantially as a hollow cylinder. The body 262 includes a lumen 264 defining a first portion of a fluid pathway. The lumen 264 includes a female taper. The lumen 264 is thus configured to receive intravenous (IV) tubing (not shown) in a friction fit. An outer surface of the body 262 includes threads 266 for optionally accommodating a male threaded Luer.

In a distal region, the taper of the lumen 264 increases sharply, creating a tapered shoulder 268 that continues to a distal end 270 of the lumen 264. A tubular member 272 extends distally from the body 262. The tubular member 272 also includes a lumen 274 that defines a second portion of the fluid pathway. At its distal end, the tubular member 272 defines an outlet 276 of the lumen 274. In the illustrated embodiment, the tubular member 272 is formed integrally as a single piece with the body 262. However, those of ordinary skill in the art will appreciate that in alternative embodiments the body 262 and the tubular member 272 could be formed as separate pieces that are secured together. The body 262 and the tubular member 272 could, for example, be welded or adhered to one another.

The connector 260 further comprises an outer collar 278 and an inner collar 280. The outer collar 278 extends distally from the body 262 and at least partially surrounds the tubular member 272. In one embodiment, the body 262 and the outer collar 278 are formed integrally as a single piece. Those of ordinary skill in the art will appreciate that in alternative embodiments the body 262 and the outer collar 278 may formed as separate pieces that are secured together. The body 262 and the outer collar 278 could, for example, be welded or adhered to one another.

In the illustrated embodiment, the outer collar 278 is shaped substantially as a cylinder. An annular space 282 separates the outer collar 278 from the tubular member 272. A distal region 284 of the outer collar 278 includes threads 286 on its internal surface. The threads 286 are configured to mate with external threads 288 on the inner collar 280. The inner collar 280 is shaped substantially as a cylinder. A distal region 290 of the inner collar 280 includes threads 292 on its internal surface. The threads 292 are configured to mate with external threads on a female connector, as described below.

A proximal end wall 294 of the outer collar 278 includes a circular groove 296. The groove 296 forms a fluid passageway that is in fluid communication with radial passageways 298 that extend substantially perpendicularly to a longitudinal axis of the connector 260. The passageways 298 may be formed in the body 262, or in the outer collar 278, or in a combination of both. Together the groove 296 and the passageways 298 form vents that facilitate priming the connector 260, as described in detail below.

As in the previous embodiments, the body 262 and the collars 278, 280 may be formed of any durable and rigid or semi-rigid materials, such as plastics. In one embodiment, for example, the body 262 and/or the collars 278, 280 may be formed of polycarbonate or polypropylene.

A porous membrane 300 abuts a distal surface of the outer collar's proximal end wall 294. In the illustrated embodiment, the porous membrane 300 is shaped as a ring having an internal diameter that is substantially equal to an external diameter of the tubular member 272 and an external diameter that is substantially equal to an internal diameter of the outer collar 278 at its proximal end wall 294. The porous membrane 300 thus covers the openings 296. As in the previous embodiments, the porous membrane 300 includes a plurality of very fine perforations that are configured to allow gaseous particles to pass through the membrane 300 and to block liquid particles from passing through the membrane 300. The membrane 300 thus provides a flow path for air, enabling the connector 260 to be primed as described below. The porous membrane 300 can be made from any of a number of suitable materials well known to those skilled in the art, such as super hydrophobic polyvinyldifluoride (PVDF).

The annular space 282 between the outer collar 278 and the tubular member 272 receives a sealing member 302. As in the previous embodiments, the sealing member 302 may be formed of any pliable and resilient material that is capable of forming a seal when abutting itself. In one embodiment, for example, the sealing member 302 may be formed of silicone.

The sealing member 302 is shaped substantially as a hollow cylinder that is open at its proximal end 304 and closed at its distal end 306. The proximal end 304 of the sealing member 302 includes a substantially disk-shaped base 308 having an aperture 310 that receives the tubular member 272 in close engagement. A first ring-shaped boss 312 around the outer surface of the base 308 seats within an annular recess 314 in the inner surface of the outer collar 278 adjacent its proximal end wall 294. A second ring-shaped boss 316 around the inner surface of the base 308 seats within an annular recess 318 in the outer surface of the tubular member 272 adjacent its proximal end. Engagement of the bosses 312, 316 and the recesses 314, 318 assists in maintaining the position of the proximal end of the sealing member 302 within the annular space 282.

The base 308 of the sealing member 302 further includes a circular groove 320 that forms a fluid passageway. The groove 320 is in fluid communication with the groove 296 in the outer collar's proximal end wall 294 through the porous membrane 300. The groove 320 is further in fluid communication with an interior space 322 of the sealing member 302 adjacent the base 308. While not visible in FIG. 12, the base 308 includes a plurality of longitudinal passageways and a plurality of radial passageway's that connect the interior space 322 with the groove 320. The passageways and groove 320 thus provide a fluid path through the base 308 that facilitates priming the connector 260, as discussed in further detail below.

The sealing member 302 at least partially surrounds the tubular member 272, including the outlet 276. However, the sealing member 302 is spaced from the tubular member 272 along its length and at the outlet 276. Sidewalls 324 of the sealing member 302 curve inwardly in an intermediate region of the sealing member 302. The distal end wall 306 of the sealing member 302 includes a slit 326. The slit 326 is sealed in the closed configuration of FIG. 11. However, the sidewalls of the slit 326 may be manually separated as described below to enable fluid to flow out of the outlet 276 and into a female connector.

The curvature of the sidewalls 324 stiffens the sidewalls 324 against expansion when fluid pressure within the sealing member 302 rises, as when the connector 260 is being primed. The curvature of the sidewalls 324 also advantageously contributes to a reduced likelihood of leaking during priming when the fluid pressure inside the sealing member 302 may be high. As the fluid pressure inside the sealing member 302 increases, any outward expansion of the sidewalls 324 in the area of the curvature creates a lever effect at the distal end 306 of sealing member 302. The lever effect tightens the slit 326, reducing the likelihood of leaking. While the illustrated embodiment shows the sidewalls 324 including an inward curvature, those of ordinary skill in the art will appreciate that in alternative embodiments the sidewalls 324 could have other shapes, such as straight, or even outwardly curved.

In use, the connector 260 receives IV tubing (not shown) in the body lumen 264. To prime the connector 260, the operator first connects IV tubing of the connector 260 to a source of IV liquid. The operator then holds the connector 260 at an elevation beneath the source of IV liquid (such as an IV bag). The liquid flows into the fluid pathway 264, 274, forcing the air distally through the fluid pathway 264, 274 and out the outlet 276 of the tubular member 272. The air then travels proximally along the outside of the tubular member 272, through the passageways 320 in the base 308, through the porous membrane 300, through the vents 296, 298 and finally to the ambient atmosphere. The vents thus facilitate priming by enabling fluid pressure within the connector 260 to stabilize with the ambient pressure.

The sealing member 302 further includes a pressure valve 328 that closes off the flow path through the passageways 320 in the event of a pressure buildup inside the connector 260. The valve 328 comprises a thin annular flange 330 extending inwardly from the sidewalls 324 of the sealing member 302. The flange 330 extends toward, but does not touch, an outer surface of the tubular member 272. The flange is positioned just distally of an external annular shoulder 332 on the tubular member 272. If pressure builds up in the space between the sealing member 302 and the tubular member 272 distal of the flange 330, the flange 330 deforms proximally until it contacts the shoulder 332, forming a seal at the shoulder 332 that blocks passage of fluid toward the passageways 320. This seal is advantageous to prevent liquid from leaking through the vents 296, 320 when the material of the porous membrane 300 is not able to withstand high fluid pressure.

Figure 13:
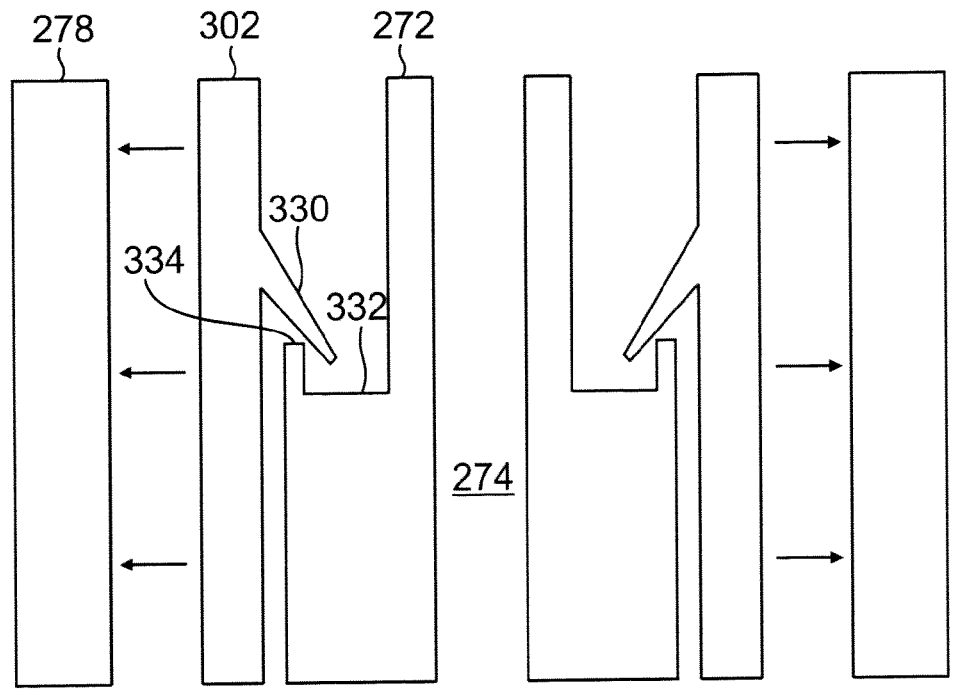
FIG. 13 is a schematic detail view of one embodiment of a pressure seal in the area of the connector of FIG. 12 indicated by the circle labeled "DETAIL VIEWS;"

FIGS. 13-16 illustrate additional possible configurations for the pressure valve 328. In FIG. 13, the annular shoulder 332 on the tubular member 272 includes a raised rim 334 that extends underneath the flange 330 on the sealing member 302. When pressure builds up inside the sealing member 302, the pliable material of the sealing member 302 expands as indicated by the arrows in FIG. 13. This expansion, coupled with fluid pressure bearing on the distal surface of the flange 330, forces the flange 330 into contact with the rim 332, creating a seal.

Figure 14:
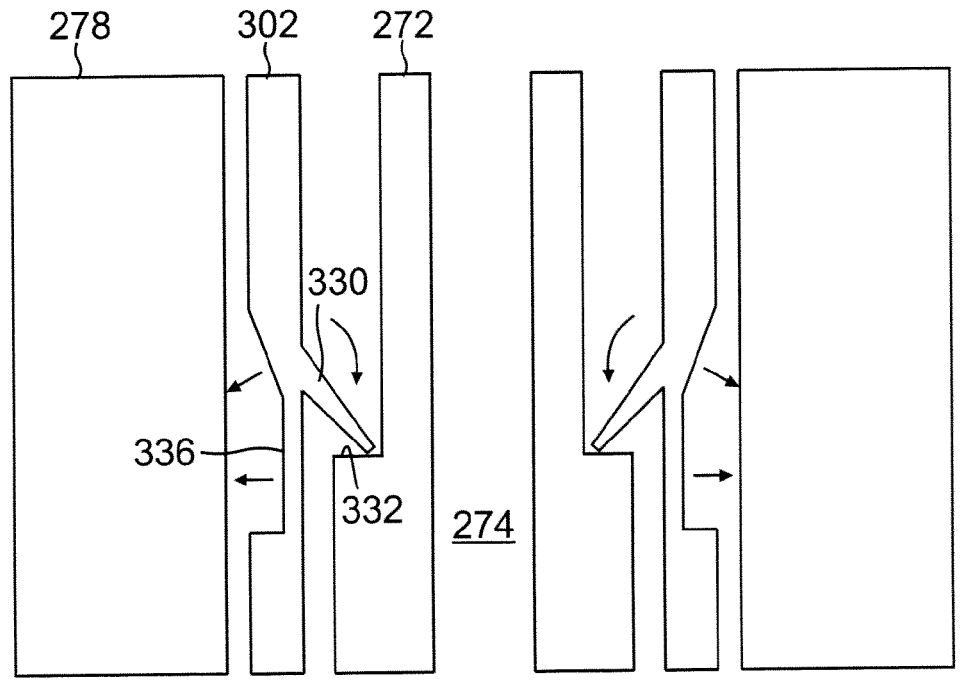
FIG. 14 is a schematic detail view of another embodiment of a pressure seal in the area of the connector of FIG. 12 indicated by the circle labeled "DETAIL VIEWS;"

In FIG. 14, the sealing member 302 includes a reduced wall thickness in a region 336 proximal of the flange 330. The reduced wall thickness facilitates flexing of the flange 330 so that it can easily deform and contact the annular shoulder 332 on the tubular member 272.

Figure 15:
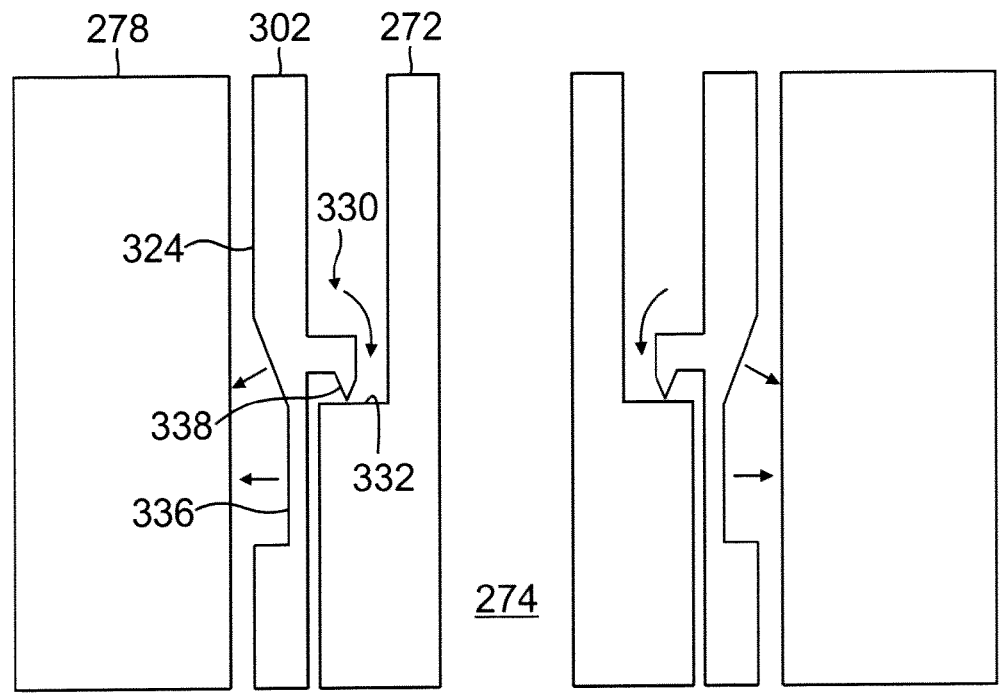
FIG. 15 is a schematic detail view of another embodiment of a pressure seal in the area of the connector of FIG. 12 indicated by the circle labeled "DETAIL VIEWS.

In FIG. 15, the sealing member 302 again includes a reduced wall thickness in a region 336 proximal of the flange 330. However, the flange 330 includes a different cross-sectional shape. The flange 330 extends inwardly substantially perpendicularly to the longitudinal axis of the sealing member 302. In addition, a triangular lip 338 extends proximally from the flange 330 at a location spaced inwardly from the sidewalls 324 of the sealing member 302. The lip 338 provides a sealing surface that bears against the annular flange 332 on the tubular member 272 when pressure builds up distally of the flange 330.

Figure 16:
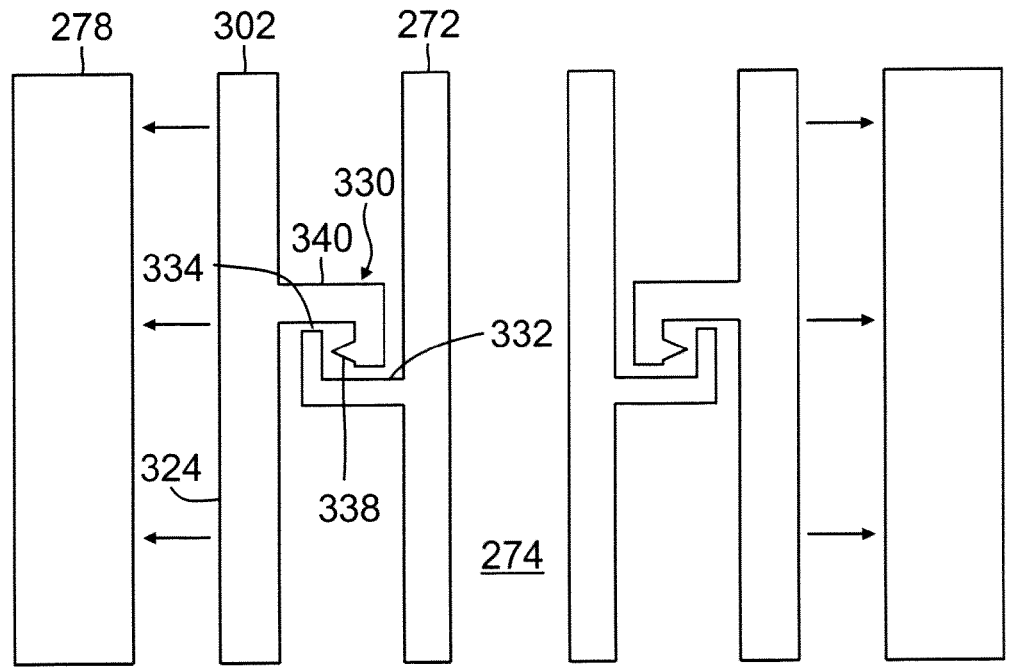
" and FIG. 16 is a schematic detail view of another embodiment of a pressure seal in the area of the connector of FIG. 12 indicated by the circle labeled "DETAIL VIEWS;"

In FIG. 16, the annular shoulder 332 on the tubular member 272 again includes a raised rim 334 that extends underneath the flange 330 on the sealing member 302. The flange 330 includes an L-shaped section 340 that extends inwardly and then proximally from the sidewalls 324 of the sealing member 302. A triangular lip 338 extends outwardly from an end of the L-shaped section 340 spaced from the sidewalls 324 of the sealing member 302. When pressure builds up distally of the flange 330, the lip 338 is forced outward to bear against the rim 334 around the annular flange 330, creating a seal.

To connect the male connector 260 of FIG. 12 to a female connector, an operator positions the distal end of the inner collar 280 in contact with the proximal end of the female connector. While FIG. 12 does not illustrate a female connector, the female connector may be similar in structure to the female connectors illustrated in the foregoing figures. The distal face 306 of the sealing member 302 bears against a proximal face of a sealing member in the female connector. The distal face of the sealing member 302 also bears against a proximal rim of a rigid housing of the female connector. The housing includes external threads configured to mate with the internal threads 292 in the distal region 290 of the inner collar 280.

To engage the threads, the operator applies digital pressure to advance the inner collar 280 toward the rigid housing on the female connector. As the two components move closer together, the rigid housing forces the sealing member 302 to deform inwardly into the inner collar 280. When the sealing member 302 has been pushed inwardly sufficiently, the internal threads 292 on the inner collar 280 engage the external threads on the female connector. To continue advancing, the operator twists the inner collar 280 relative to the female connector. In one embodiment, the threaded engagement between the outer collar 278 and the inner collar 280 may offer greater frictional resistance than the threaded engagement between the inner collar 280 and the female connector. The operator can thus induce relative twisting of the inner collar 280 and the female connector while grasping the outer collar 278 in one hand and the female connector in the other hand, rather than grasping the inner collar 280 and the female connector. This feature eases the task of securing the inner collar 280 to the female connector, because the operator can grasp the larger surface area of the outer collar 278.

When the inner collar 280 has been completely screwed onto the female connector, the proximal rim of the female connector housing contacts a distal face 342 of an inwardly extending flange located proximally of the threads 292 of the inner collar 280. At this point, relative rotation of the inner collar 280 and the female connector ceases. The distal region 344 of the sealing member 302 is deformed into the inner collar 280 toward the outlet 276 of the tubular member 272. The sealing member 302 also bears against the sealing member in the female connector, deforming it. The deformed sealing members maintain a seal at the connection of the inner collar 280 and the female connector.

To open fluid communication between the two connectors, the operator continues to apply a twisting force to the outer collar 278 and the female connector. Since the female connector cannot advance any farther into the inner collar 280, the inner collar 280 begins twisting relative to the outer collar 278. Engagement of the external threads 288 on the inner collar 280 with the internal threads 286 on the outer collar 278 causes the inner collar 280 to advance proximally into the outer collar 278. At the same time, the outlet 276 of the tubular member 272 advances through the slits in the sealing members, opening fluid communication between the two connectors.

Figure 17:
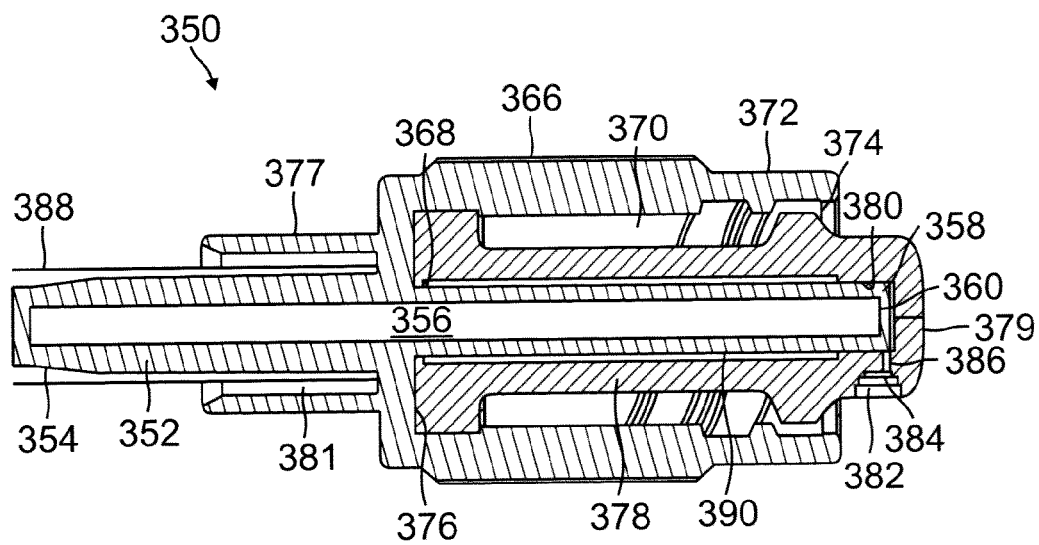
FIG. 17 is a side cross-sectional view of another embodiment of the present selectively sealable male needleless connector.

FIG. 17 illustrates another embodiment of the present selectively sealable male needleless connector 350. The connector 350 is similar to the embodiment described above and illustrated in FIG. 11. However, the connector 350 of FIG. 17 includes a body having an elongate tubular member 352. At least a proximal end 354 of the tubular member 352 includes a male taper. The tubular member 352 is thus configured to receive intravenous (IV) tubing 356 in a friction fit around the outside of the tubular member 352. The tubular member 352 defines a lumen 356. In contrast to the embodiment of FIG. 11, the lumen 356 has a constant inside diameter. At its distal end 358, the tubular member 352 defines an outlet 360 of the lumen 356.

A cylindrical collar 366 extends distally from a medial portion 368 of the body and partially surrounds the tubular member 352. An annular space 370 separates the collar 366 from the tubular member 352. A distal region 372 of the collar 366 includes threads 374 on its internal surface. The threads 374 are configured to mate with external threads on a female connector (not shown) in the same manner as described above with respect to the connector 210 of FIG. 11.

A proximal wall 376 of the collar 366 is solid, in contrast to the proximal wall of the collar 228 of FIG. 11, which includes apertures 238 and passageways 240 for venting air. In the illustrated embodiment, the collar 366 is formed integrally as a single piece with the body 352. However, those of ordinary skill in the art will appreciate that in alternative embodiments the body 352 and the collar 366 could be formed as separate pieces. A cylindrical shroud 377 extends proximally from the proximal wall of the collar 366, partially surrounding the tubular member 352. An annular space 381 between the interior of the shroud 377 and the exterior of the tubular member 352 receives the IV tubing 388. Adhesive may be applied within the annular space 381 to strengthen the connection between the IV tubing 388 and the tubular member 352.

As in the previous embodiments, the body 352 and the collar 366 may be formed of any durable and rigid or semi-rigid materials, such as plastics. In one embodiment, for example, the body 352 and/or the collar 366 may be formed of polycarbonate or polypropylene.

The annular space 370 between the collar 366 and the tubular member 352 receives a sealing member 378. As in the previous embodiments, the sealing member 378 may be formed of any pliable and resilient material that is capable of forming a seal when abutting itself. In one embodiment, for example, the sealing member 378 may be formed of silicone.

The sealing member 378 is shaped substantially the same as the sealing member 244 of FIG. 11. However, in contrast to the sealing member 244 of FIG. 11, a distal end 379 of the sealing member 378 includes a reduced diameter 380. The reduced diameter 380 hugs the exterior of the tubular member 352 at its distal end 358 in a tight or interference fit. The reduced diameter 380 thus forms a liquid-tight seal against the exterior of the tubular member 352.

At its distal end 379, an exterior surface of the sealing member 378 includes a recess 382 that receives a porous membrane 384. A passageway 386 extends from the recess 382 to the interior of the sealing member 378. The passageway 386, porous membrane 384 and recess 382 define a fluid pathway. However, as in the previous embodiments, the porous membrane 384 includes a plurality of very fine perforations that are configured to allow gaseous particles to pass through the membrane and to block liquid particles from passing through the membrane. The porous membrane 384 thus provides a flow path for air, enabling the connector 350 to be primed as described below. The porous membrane 384 can be made from any of a number of suitable materials well known to those skilled in the art, such as super hydrophobic polyvinyldifluoride (PVDF).

To prime the connector 350, the operator first connects IV tubing 388 of the connector 350 to a source of IV liquid (such as an IV bag). The operator then holds the connector 350 at an elevation beneath the source of IV liquid. The liquid flows into the lumen 356, forcing the air in the lumen 356 distally. The air is forced through the passageway 386, through the porous membrane 384, and out through the recess 382 to the ambient atmosphere.

The process for connecting the male connector 350 of FIG. 17 to a female connector is similar to the process described above for connecting the male connector 210 of FIG. 11 to a female connector. However, when the sealing member 378 collapses into the annular space 370, the reduced diameter 380 of the distal end 379 remains in sealing contact with the exterior of the tubular member 352. The seal resists leakage of IV fluid into the annular space 390 between the sealing member 378 and the tubular member 352 proximal of the reduced diameter 380. The seal thus reduces the volume of dead space within the connector 350 where stagnant fluid may collect.

Figure 18:
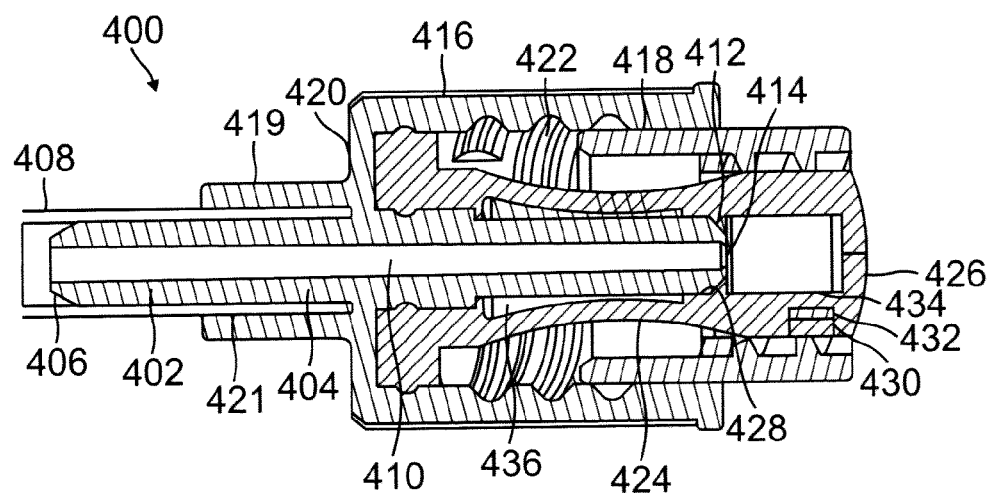
FIG. 18 is a side cross-sectional view of another embodiment of the present selectively sealable male needleless connector.

FIG. 18 illustrates another embodiment of the present selectively sealable male needleless connector 400. The connector 400 is similar to the embodiment described above and illustrated in FIG. 12. However, the connector 400 of FIG. 18 includes a body 402 having an elongate tubular member 404. At least a proximal end 406 of the tubular member 404 includes a male taper. The tubular member 404 is thus configured to receive intravenous (IV) tubing 408 in a friction fit around the outside of the tubular member 404. The tubular member 404 defines a lumen 410. In contrast to the embodiment of FIG. 12, the lumen 410 has a smooth taper on its inside diameter, tapering down from the proximal end 406 to the distal end 412. At its distal end 412, the tubular member 404 defines an outlet 414 of the lumen 410.

The connector 400 further comprises a cylindrical outer collar 416 and a cylindrical inner collar 418. The inner and outer collars 418, 416 are similar in structure and function to the outer and inner collars 278, 280 described above and illustrated in FIG. 12. However, a proximal wall 420 of the outer collar 416 is solid, in contrast to the proximal end wall 294 of the outer collar 278 of FIG. 12, which includes a groove 296 and passageways 298 for venting air. In the illustrated embodiment, the outer collar 416 is formed integrally as a single piece with the body 402. However, those of ordinary skill in the art will appreciate that in alternative embodiments the body 402 and the outer collar 416 could be formed as separate pieces.

A cylindrical shroud 419 extends proximally from the proximal wall of the collar 420, partially surrounding the tubular member 404. An annular space 421 between the interior of the shroud 419 and the exterior of the tubular member 404 receives the IV tubing 408. Adhesive may be applied within the annular space 421 to strengthen the connection between the IV tubing 408 and the tubular member 404.

As in the previous embodiments, the body 402 and the outer collar 416 may be formed of any durable and rigid or semi-rigid materials, such as plastics. In one embodiment, for example, the body 402 and/or the outer collar 416 may be formed of polycarbonate or polypropylene.

The annular space 422 between the outer collar 416 and the tubular member 404 receives a sealing member 424. As in the previous embodiments, the sealing member 424 may be formed of any pliable and resilient material that is capable of forming a seal when abutting itself. In one embodiment, for example, the sealing member 424 may be formed of silicone.

The sealing member 424 is shaped substantially the same as the sealing member 302 of FIG. 12. However, in contrast to the sealing member 302 of FIG. 12, a distal end 426 of the sealing member 424 includes a reduced diameter 428. The reduced diameter 428 hugs the exterior of the tubular member 404 at its distal end 412 in a tight or interference fit. The reduced diameter 428 thus forms a liquid-tight seal against the exterior of the tubular member 404.

At its distal end 426, an exterior surface of the sealing member 424 includes a recess 430 that receives a porous membrane 432. A passageway 434 extends from the recess 430 to the interior of the sealing member 424. The passageway 434, porous membrane 432 and recess 430 define a fluid pathway. However, as in the previous embodiments, the porous membrane 432 includes a plurality of very fine perforations that are configured to allow gaseous particles to pass through the membrane and to block liquid particles from passing through the membrane. The porous membrane 432 thus provides a flow path for air, enabling the connector 400 to be primed as described below. The porous membrane 432 can be made from any of a number of suitable materials well known to those skilled in the art, such as super hydrophobic polyvinyldifluoride (PVDF).

To prime the connector 400, the operator first connects IV tubing 408 of the connector 400 to a source of IV liquid (such as an IV bag). The operator then holds the connector 400 at an elevation beneath the source of IV liquid. The liquid flows into the lumen 410, forcing the air in the lumen 410 distally. The air is forced through the passageway 434, through the porous membrane 432, and out through the recess 430 to the ambient atmosphere.

The process for connecting the male connector 400 of FIG. 18 to a female connector is similar to the process described above for connecting the male connector 260 of FIG. 12 to a female connector. However, when the sealing member 424 collapses into the annular space 422, the reduced diameter 428 of the distal end 426 remains in sealing contact with the exterior of the tubular member 404. The seal resists leakage of IV fluid into the space 436 between the sealing member 424 and the tubular member 404 proximal of the reduced diameter 428. The seal thus reduces the volume of dead space within the connector 400 where stagnant fluid may collect.

Figure 19:
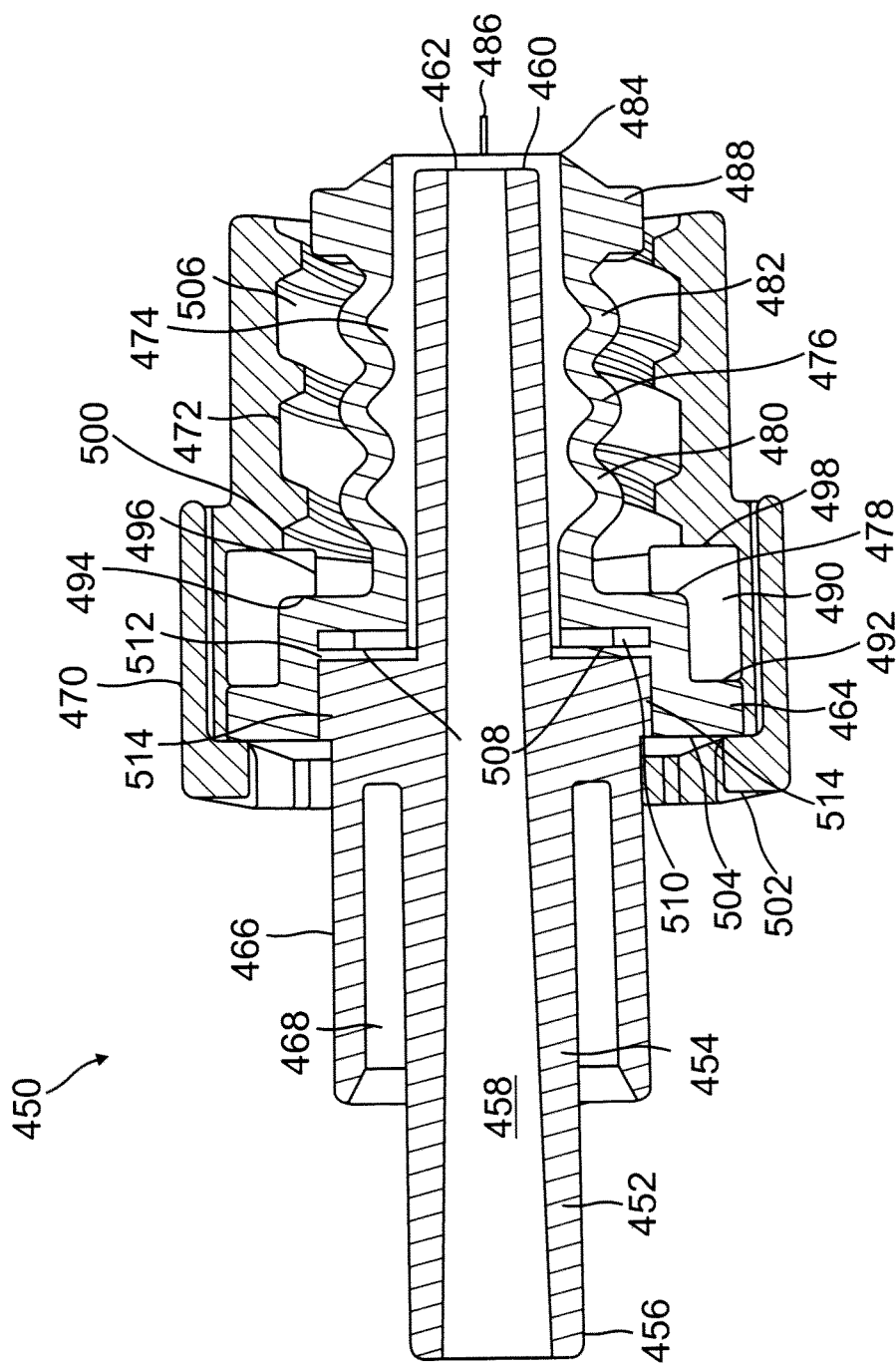
FIG. 19 is a side cross-sectional view of another embodiment of the present selectively sealable male needleless connector.

FIG. 19 illustrates another embodiment of the present selectively sealable male needleless connector 450. The connector 450 includes a body 452 having an elongate tubular member 454. At least a proximal end 456 of the tubular member 454 includes a male taper. The tubular member 454 is thus configured to receive intravenous (IV) tubing (not shown) in a friction fit around the outside of the tubular member 454. The tubular member 454 defines a lumen 458. The lumen 458 has a smooth taper on its inside diameter, tapering down from the proximal end 456 to the distal end 460. At its distal end 460, the tubular member 454 defines an outlet 462 of the lumen 458.

The body 452 includes a disk shaped flange 464 extending radially outward from its medial region. A cylindrical shroud 466 extends proximally from the flange 464, partially surrounding the tubular member 454. An annular space 468 between the interior of the shroud 466 and the exterior of the tubular member 454 receives the IV tubing. Adhesive may be applied within the annular space 468 to strengthen the connection between the IV tubing and the tubular member 454.

A cylindrical collar 470 engages the flange 464 and partially surrounds the body 452 distally of the flange 464. An interior surface of the collar 470 includes threads 472 configured to engage external threads on a female connector (not shown), as described below. An annular space 474 between the collar 470 and the tubular member 454 receives a sealing member 476. As in the previous embodiments, the sealing member 476 may be formed of any pliable and resilient material that is capable of forming a seal when abutting itself. In one embodiment, for example, the sealing member 476 may be formed of silicone.

The sealing member 476 includes a substantially disk shaped base 478 at its proximal end. A generally cylindrical sleeve portion 480 extends distally from the base 478 and surrounds a distal region of the tubular member 454. A sidewall of the sleeve portion 480 includes accordion-like corrugations 482. The corrugations 482 create natural flex points for the sealing member 476 so that it can collapse easily and predictably when the connector 450 is secured to a female connector, as described below.

A distal end 484 of the sealing member 476 includes a slit 486 through which the tubular member 454 may protrude when the connector 450 is secured to a female connector. Proximally of the slit 486, the distal end 484 of the sealing member 476 further includes a disk shaped flange 488 that engages a shroud on the female connector and assists the shroud in pushing the sealing member 476 proximally within the annular space 474 to collapse the sealing member 476 and extend the tubular member 454 through the slit 486.

The connector 450 further comprises a locking ring 490 positioned within the collar 470 and abutting a distal surface 492 of the flange 464 with the base 478 of the sealing member 476 sandwiched in between. The locking ring 490 includes an inwardly extending flange 494 at its distal end that abuts a distal face 496 of the base 478 of the sealing member 476, thereby resisting distal movement of the sealing member 476. An interior surface of the collar 470 includes an annular shoulder 498 that faces proximally and abuts a distal surface 500 of the locking ring 490, thereby resisting distal movement of the locking ring 490. A proximal end of the collar 470 similarly includes a plurality of inwardly extending tabs 502 that abut a proximal face 504 of the flange 464 on the body 452, thereby sandwiching the body 452 and the locking ring 490 with the locking ring 490 holding the base 478 of the sealing member 476 against the flange 464.

The body 452, the collar 470 and the locking ring 490 may be formed of any durable and rigid or semi-rigid materials, such as plastics. In one embodiment, for example, these components may be formed of polycarbonate or polypropylene.

An inside diameter of the sealing member sleeve portion 480 is greater than an outside diameter of the tubular member 454. The sleeve portion 480 and the tubular member 454 thus define a substantially annular space 506 between them. The distal end 484 of the sealing member 476 is also spaced from the outlet 462 at the distal end 460 of the tubular member 454. There is thus a fluid pathway from the lumen 458 through the outlet 462 and around the outside of the tubular member 454. In its base 478, the sealing member 476 includes a plurality of radial passages 508 that fluidly connect the annular space 506 with a circular groove 510 in the base 478. The fluid pathway thus continues through the base 478 via the radial passages 508 and the groove 510.

A disk shaped porous membrane 512 abuts a proximal surface of the base 478 and covers the circular groove 510 in the base 478. A plurality of longitudinal passages 514 in the flange 464 of the body 452 align with the circular groove 510 in the base 478 opposite the porous membrane 512. The fluid pathway through the connector 450 thus continues from the groove 510 through the porous membrane 512 and out to the ambient atmosphere through the longitudinal passages 514. However, as in the previous embodiments, the porous membrane 512 includes a plurality of very fine perforations that are configured to allow gaseous particles to pass through the membrane and to block liquid particles from passing through the membrane. The porous membrane 512 thus provides a flow path for air, enabling the connector 450 to be primed as described below. The porous membrane 512 can be made from any of a number of suitable materials well known to those skilled in the art, such as super hydrophobic polyvinyldifluoride (PVDF).

To prime the connector 450, the operator first connects IV tubing of the connector 450 to a source of IV liquid (such as an IV bag). The operator then holds the connector 450 at an elevation beneath the source of IV liquid. The liquid flows into the lumen 458, forcing the air in the lumen 458 distally. The air is forced through the outlet 462, proximally around the outside of the tubular member 454, through the radial passageways 508 and the groove 510, through the porous membrane 512, and out through the longitudinal passages 514 to the ambient atmosphere.

Figure 20:
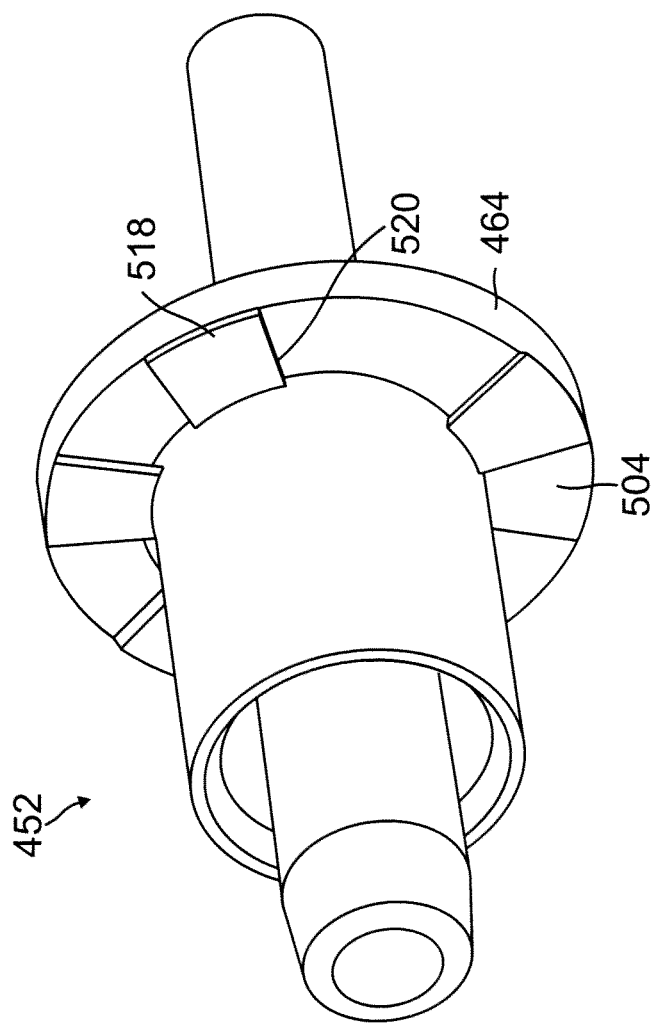
FIG. 20 is a proximal perspective view of the body of the connector of FIG. 19.
Figure 21:
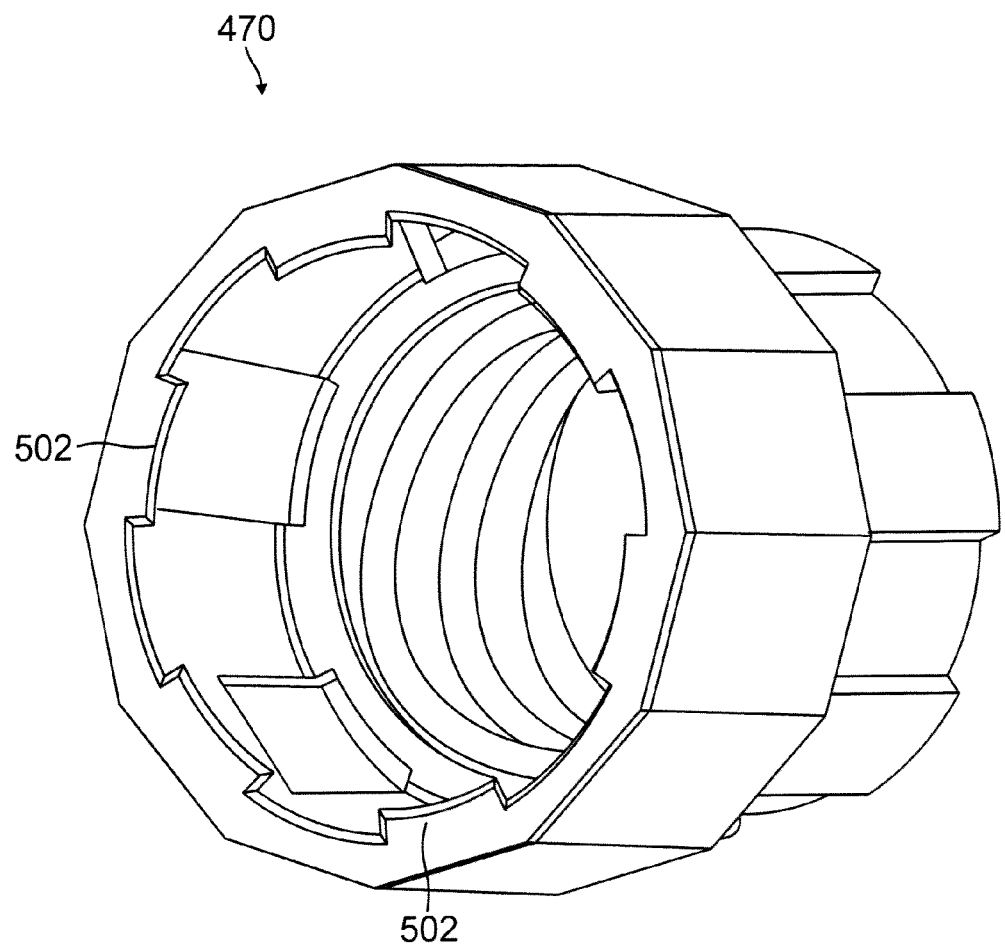
FIG. 21 is a proximal perspective view of the collar of the connector of FIG. 19.

FIGS. 20 and 21 illustrate the body 452 and the collar 470, respectively, in greater detail. With reference to FIG. 20, the proximal face 504 of the body flange 464 includes a plurality of ramps 518. Each ramp 518 includes a sloped surface that rises gradually to a ledge or an abrupt drop off 520. Each of the ramps 518 is oriented to slope in the same direction. With reference to FIG. 21, the proximal end of the collar 470 includes a plurality of inwardly extending tabs 502. The tabs 502 abut the proximal face 504 of the body flange 464, as shown in FIG. 19. The tabs 502 are configured to ride up and over the ramps 518 when the collar 470 is rotated with respect to the body 452. As the tabs 502 ride over the abrupt drop offs 520 of the ramps 518, the operator hears a clicking sound and feels a tactile sensation. The sound and feel of the clicking tells the operator that the connector 450 is fully secured to a female connector, as described more fully below.

The process for connecting the male connector 450 of FIG. 19 to a female connector is similar to the process described above for connecting the male connector 210 of FIG. 11 to a female connector. However, the operator preferably grips the outside of the collar 470 with a first hand and the female connector with a second hand. Relatively rotating the connectors causes a shroud of the female connector to advance into the annular space 474. Initially, the collar 470 and the body 452 rotate together with respect to the sealing member 476. However, as the female connector advances, it pushes against the flange 488 at the distal end of the sealing member 476, thereby compacting the sealing member 476 into the annular space 474. As the compaction increases, so does a friction force between the sealing member 476 and the female connector. As described above, the sealing member 476 is preferably constructed of a resilient material, such as silicone. Such materials generally have a high coefficient of friction relative to more rigid materials, such as polycarbonate or polypropylene. Thus, as the friction force between the sealing member 476 and the female connector rises, it eventually reaches a threshold at which the friction between the sealing member 476 and the female connector is greater than a friction force at the junction between the collar 470 and the body flange 464 and locking ring 490. At that threshold, the body 452 and the female connector stop rotating relative to one another and the body 452 and the locking ring 490 begin rotating relative to the collar 470. That relative rotation causes the tabs 502 on the collar 470 to ride over the ramps 518 on the body flange 464, inducing the clicking and tactile sensation described above. When the clicking begins, the operator knows that the connection is secure.

Figure 22:
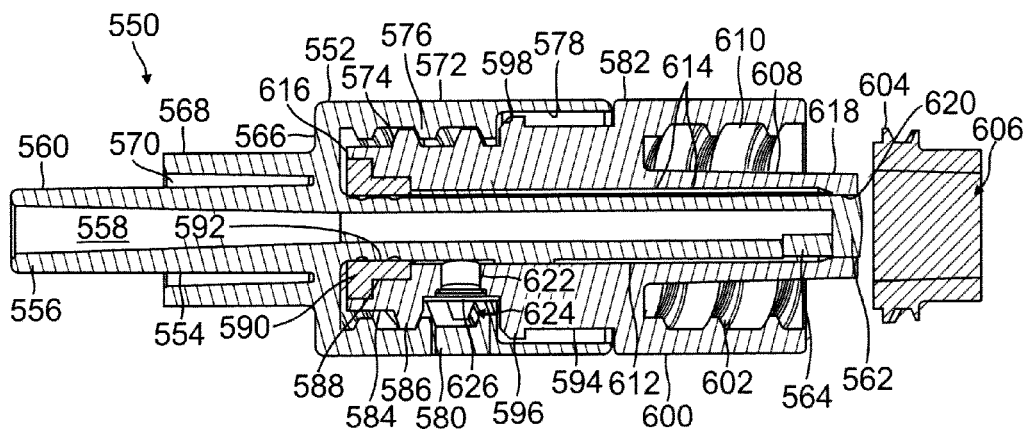
FIG. 22 is a side cross-sectional view of another embodiment of the present selectively sealable male needleless connector, showing the connector disconnected from a female connector.

FIG. 22 illustrates another embodiment of the present selectively sealable male needleless connector 550. The connector 550 includes a proximal body 552 shaped substantially as a stepped cylinder. The proximal body 552 includes an elongate tubular member 554. A proximal end 556 of the tubular member 554 is configured to receive intravenous (IV) tubing (not shown) in a friction fit around the outside of the tubular member 554. The tubular member 554 defines a lumen 558. A proximal portion 560 of the lumen 558 has a smooth taper on its inside diameter, tapering down from a proximal end to a medial portion. The remaining portion of the lumen 558 includes a constant diameter that extends to a distal end 562 of the tubular member 554. Adjacent the distal end 562, a sidewall of the tubular member 554 includes an opening that defines an outlet 564 of the lumen 558.

A disk shaped flange 566 extends radially outward from a medial region of the tubular member 554. A cylindrical shroud 568 extends proximally from the flange 566, partially surrounding the tubular member 554. An annular space 570 between the interior of the shroud 568 and the exterior of the tubular member 554 receives the IV tubing. Adhesive may be applied within the annular space 570 to strengthen the connection between the IV tubing and the tubular member 554.

A cylindrical collar 572, hereinafter referred to as the proximal collar 572, extends distally from a periphery of the flange 566 and partially surrounds the tubular member 554 distally of the flange 566. A proximal portion 574 of an interior surface of the proximal collar 572 includes threads 576. A distal portion 578 of the interior surface of the proximal collar 572 is smooth. In the threaded portion 574, a sidewall of the collar includes an aperture 580, the function of which is described below.

The connector 550 further includes a distal body 582 shaped substantially as a stepped cylinder. The distal body 582 includes a proximal portion 584 having external threads 586. The external threads 586 engage the internal threads 576 on the proximal collar 572 so that the proximal and distal bodies 552, 582 are rotatable with respect to one another. The threaded engagement also produces relative translation of the bodies 552, 582 when they are rotated with respect to one another. A proximal end of the distal body 582 includes a recess 588 shaped as a stepped cylinder. The recess 588 receives a complimentary shaped elastomeric sealing member 590. The sealing member 590 includes a cylindrical passage 592 that receives the exterior of the tubular member 554 in sealing engagement. The sealing member 590 may be formed of any pliable and resilient material that is capable of forming a seal when abutting the tubular member 554. In one embodiment, for example, the sealing member 590 may be formed of silicone.

The distal body 582 further comprises a medial portion 594 that is shaped as a smooth cylinder having a proximal flange 596 extending radially outward. The medial portion 594 is received within the distal portion 578 of the proximal collar 572. A juncture of the proximal and distal portions 574, 578 of the proximal collar 572 includes an inwardly extending annular shoulder 598. The shoulder 598 provides an abutment point for the flange 596 on the medial portion 594 that limits the travel of the distal body 582 into the proximal collar 572.

A cylindrical collar 600, hereinafter referred to as the distal collar 600, extends distally from a periphery of the medial portion 594 of the distal body 582. An interior surface of the distal collar 600 includes threads 602. The threads 602 are configured to engage external threads 604 on a female connector 606, as described below. A cylindrical nozzle 608 extends distally from the medial portion 594 of the distal body 582. The distal collar 600 partially surrounds the nozzle 608 with an annular space 610 defined in between.

The proximal and distal bodies 552, 582 may be formed of any durable and rigid or semi-rigid materials, such as plastics. In one embodiment, for example, these components may be formed of polycarbonate or polypropylene.

The distal body 582 includes a central longitudinal passageway 612 that receives the tubular member 554. Except as described below, substantially the entire length of the tubular member 554 includes a constant exterior diameter. Similarly, except as described below substantially the entire length of the longitudinal passageway 612 includes a constant interior diameter. Further, again except as described below, the interior diameter of the longitudinal passageway 612 is slightly greater than the exterior diameter of the tubular member 554. The longitudinal passageway 612 and the tubular member 554 thus define an annular space 614 between them.

The recess 588 at the proximal end 616 of the longitudinal passageway 612 receives the sealing member 590. The sealing member 590 includes an interior diameter that substantially corresponds to the exterior diameter of the tubular member 554, thus forming a liquid tight seal around the tubular member 554. At the distal end 618 of the longitudinal passageway 612, the nozzle 608 includes a reduced interior diameter 620 that substantially corresponds to the exterior diameter of the tubular member 554, thus forming a liquid tight seal around the tubular member 554 at the distal end 562. The reduced interior diameter 620 is positioned distally of the outlet 564 in the tubular member 554, so that the lumen 558 is in fluid communication with the annular space 614 through the outlet 564. However, liquid in the annular space 614 does not leak out the distal end 618 of the nozzle 608, due to the seal formed around the distal end 562 of the tubular member 554 by the reduced interior diameter 620.

The threaded proximal portion 584 of the distal body 582 includes a radial through hole comprising a vent 622. The vent 622 is in fluid communication with the annular space 614. A recess 624 in the exterior surface of the proximal portion 584 receives a porous membrane 626 that covers the vent 622. As in the previous embodiments, the porous membrane 626 includes a plurality of very fine perforations that are configured to allow gaseous particles to pass through the membrane and to block liquid particles from passing through the membrane. The porous membrane 626 thus provides a flow path for air, enabling the connector 550 to be primed as described below. The porous membrane 626 can be made from any of a number of suitable materials well known to those skilled in the art, such as super hydrophobic polyvinyldifluoride (PVDF).

To prime the connector 550, the operator begins with the connector 550 in the configuration of FIG. 22 in which the distal body 582 is advanced entirely, or substantially entirely, within the proximal collar 572. In this configuration, the vent 622 and porous membrane 626 align with the aperture 580 in the proximal collar 572. The operator then connects IV tubing of the connector 550 to a source of IV liquid (such as an IV bag). The operator then holds the connector 550 at an elevation beneath the source of IV liquid. The liquid flows into the lumen 558, forcing the air in the lumen 558 distally. The air is forced through the outlet 564, proximally around the outside of the tubular member 554, through the vent 622, through the porous membrane 626, and out through the aperture 580 to the ambient atmosphere.

Figure 23:
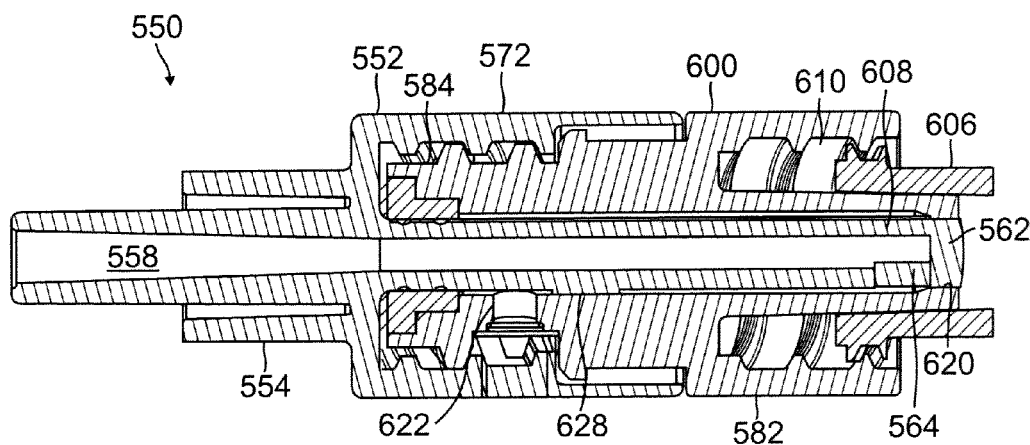
FIG. 23 is a side cross-sectional view of the connector of FIG. 22, showing the connector connected to a female connector in a closed flow configuration.

FIG. 23 illustrates the connector 550 connected to a female connector 606 in a closed flow configuration. In this configuration, the female connector 606 is received within the annular space 610 between the distal collar 600 and the nozzle 608. However, no liquid flows from the male connector 550 into the female connector 606 due to the seal formed around the distal end 562 of the tubular member 554 by the reduced interior diameter 620 of the nozzle 608. The nozzle 608 includes a male taper on its exterior surface. The female connector 606 includes a mating female taper on its interior surface. Thus, the female connector 606 may be advanced as far as necessary into the annular space 610 so that the exterior of the nozzle 608 forms a seal against the interior of the female connector 606.

To open fluid flow from the male connector 550 to the female connector 606, the operator rotates the proximal and distal bodies 552, 582 relative to one another. The threaded connection between the bodies 552, 582 causes the distal body 582 to back out of the proximal collar 572 toward the configuration of FIG. 24. The operator may rotate the proximal and distal bodies 552, 582 relative to one another using at least the following techniques.

In one technique, the operator begins with the male connector 550 and female connector 606 in the disconnected configuration of FIG. 22. Grasping the proximal collar 572 with one hand and the female connector 606 with the other hand, the operator brings the connectors 550, 606 together until the internal threads 602 on the distal collar 600 engage the external threads 604 on the female connector 606. The operator then twists the proximal collar 572 and the female connector 606 in opposite directions so that the female connector 606 advances into the annular space 610. As the operator applies the twisting force to the proximal collar 572, the distal body 582 and distal collar 600 rotate in the same direction as the proximal body 552 and proximal collar 572.

Eventually, the female connector 606 ceases advancing into the annular space 610 because, for example, the exterior surface of the nozzle 608 snugly engages the interior surface of the female connector 606. At this point, continued twisting force applied to the proximal collar 572 and the female connector 606 will induce relative rotation of the proximal and distal bodies 552, 582 in opposite directions and the distal body 582 will begin to back out of the proximal collar 572. This opposite rotation and backing out occurs due to the reverse threading of the proximal collar 572 and the distal collar 600, which is visible in FIGS. 23 and 24. Further, in one embodiment the fit between the threads 576, 586 of the proximal collar 572 and distal body 582, respectively, is tighter than the fit between the threads 602, 604 of the distal collar 600 and female connector 606, respectively. Thus, as the operator applies twisting forces on the proximal collar 572 and the female connector 606, the female connector 606 advances into the distal collar 600 until it can advance no more, and only after that point the proximal and distal bodies 552, 582 begin rotating relative to one another.

Figure 24:
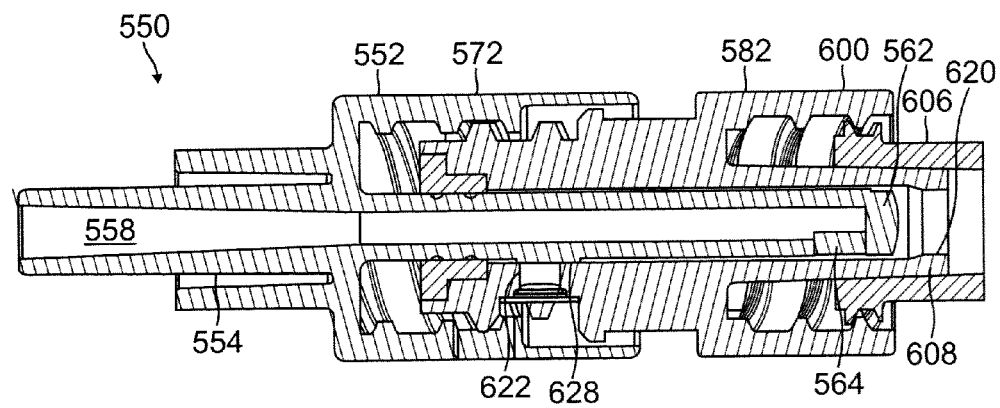
FIG. 24 is a side cross-sectional view of the connector of FIG. 22, showing the connector connected to a female connector in an open flow configuration.

With reference to FIG. 24, as the distal body 582 backs out of the proximal body 552, the tubular member 554 backs out of the nozzle 608. As contact between the distal end 562 of the tubular member 554 and the reduced interior diameter 620 of the nozzle 608 is broken, fluid communication opens between the lumen 558 and the female connector 606. In the illustrated embodiment, the exterior surface of the tubular member 554 includes a plateau 628 in its medial portion. The plateau 628 has a height such that it contacts the interior surface of the longitudinal passageway 612. In the closed flow configuration of FIG. 23, the plateau 628 is located distally of the vent 622. However, in the open flow configuration of FIG. 24, the plateau 628 covers the vent 622. The plateau 628 seals the vent 622 to reduce the likelihood of liquid leaking through the vent 622.

In another technique, the operator begins with the male connector 550 and female connector 606 in the connected configuration of FIG. 23. Grasping the proximal collar 572 with one hand and the distal collar 600 with the other hand, the operator twists the collars 572, 600 in opposite directions. Due to the reverse threading of the proximal collar 572 and the proximal portion 584 of the distal body 582, the operator applies the twisting forces in the opposite direction from the typical clockwise to tighten, counterclockwise to loosen. Applying the reverse twisting forces, the distal body 582 backs out of the proximal collar 572 similarly as described above in order to open flow from the male connector 550 to the female connector 606.

Advantageously, the present connector 550 enables flow to be closed without disconnecting the male connector 550 from the female connector 606. To close flow from the open flow configuration of FIG. 24, the operator applies oppositely directed twisting forces to the collars 572, 600 to advance the distal body 582 back into the proximal collar 572. As the distal body 582 advances into the proximal collar 572, the tubular member 554 advances farther into the nozzle 608. Eventually, the reduced interior diameter 620 of the nozzle 608 covers the distal end 562 of the tubular member 554 and seals fluid communication between the lumen 558 and the female connector 606. The operator can reopen and reclose fluid communication from the male connector 550 to the female connector 606 as many times as desired, all without having to disconnect the male connector 550 from the female connector 606. The continuous connection reduces the likelihood of contamination within the connectors.

Figure 25:
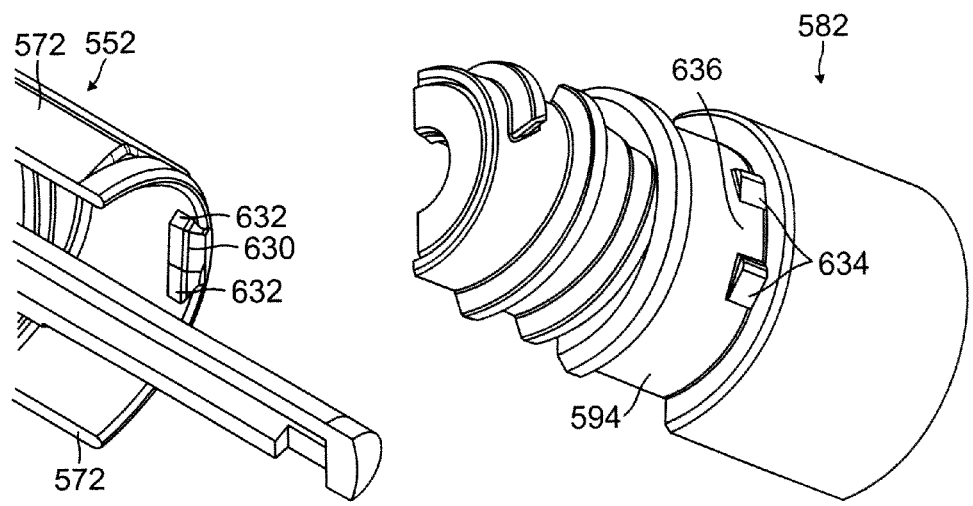
FIG. 25 is a distal perspective view of the body of the connector of FIG. 22 and a distal perspective view of the collar of the connector of FIG. 22.

FIG. 25 illustrates detail views of alternative embodiments of the proximal body 552 and the distal body 582. With reference to the left hand portion of FIG. 25, at its distal end the smooth interior surface of the proximal collar 572 includes a plateau 630 having ramped surfaces 632 at either circumferential end. With reference to the right hand portion of FIG. 25, at its distal end the smooth exterior surface of the medial portion 594 includes first and second spaced ramps 634. The plateau 630 and the ramps 634 are positioned such that when the proximal and distal bodies 552, 582 are in the closed flow configuration of FIG. 23 the plateau 630 is positioned to one side of a first one of the ramps 634, outside the space 636 between the first and second ramps 634. As the operator applies opposite twisting forces to the proximal collar 572 and the female connector 606 to open fluid flow, as described above, when the female connector 606 stops advancing into the annular space 610 the proximal and distal bodies 552, 582 begin rotating relative to one another. The relative rotation causes the plateau 630 to ride over the first one of the ramps 634 and snap into the space 636 between the ramps 634. As the plateau 630 snaps into the space 636 between the ramps 634, the operator hears a clicking sound and feels a tactile sensation. The sound and feel of the clicking tells the operator that the female connector 606 is disposed all the way in the annular space 610 and relative rotation of the proximal and distal bodies 552, 582 has begun, but the connector 550 is still in the closed flow configuration. As the operator continues to apply the twisting forces, the plateau 630 rides over the second one of the ramps 634 and snaps out of the space 636 between the ramps 634. The clicking and tactile sensation that occur at this point inform the operator that the connector 550 is moving toward the open flow configuration. While not shown, the connector 550 may include a similar ramp and plateau feature that notifies the operator when the open flow configuration has been reached. A similar feature may also notify the operator when the plateau 628 (FIG. 24) covers the vent 622. Those of ordinary skill in the art will appreciate that in embodiments including the ramp and plateau feature the threads 576 on the proximal collar 572 and the threads 586 on the proximal portion 584 of the distal body 582 need not have a tighter fit than the threads 602 on the distal collar 572 and the threads 604 on the female connector 606. The ramp 634 and plateau 630 will restrain the proximal and distal bodies 552, 582 from rotating until the female connector 606 cannot advance any farther into the annular space 610.

Figure 26:
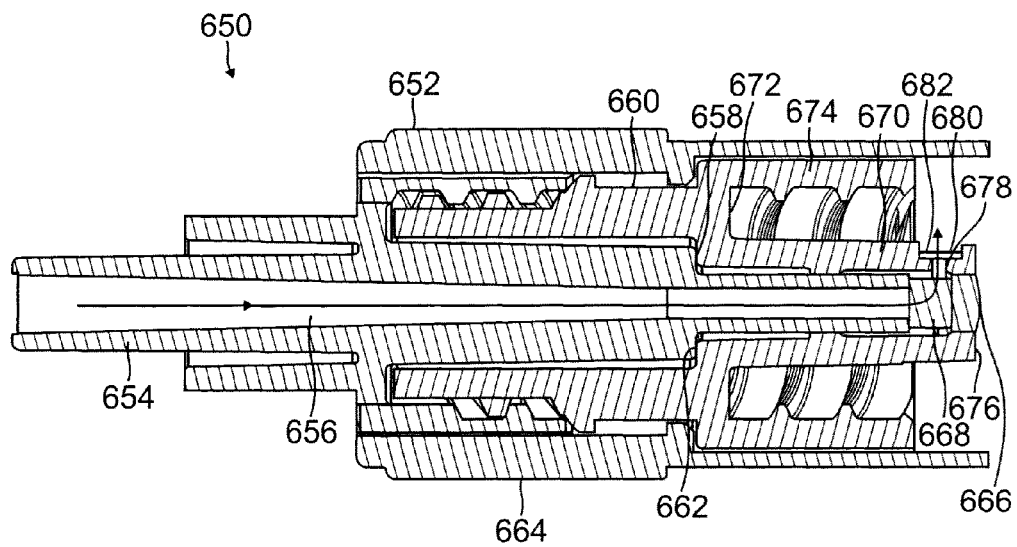
FIG. 26 is a side cross-sectional view of another embodiment of the present selectively sealable male needleless connector.
Figure 27:
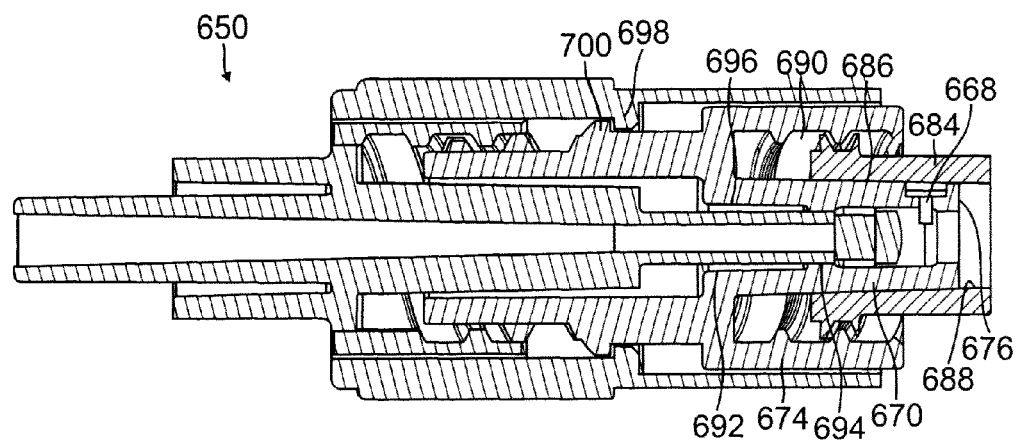
FIG. 27 is a side cross-sectional view of the connector of FIG. 26, showing the connector connected to a female connector in an open flow configuration.

FIGS. 26 and 27 illustrate another embodiment of the present selectively sealable male needleless connector 650. The connector 650 shares many similarities with the connector 550 described above and shown in FIG. 22. Accordingly, the description herein will focus on those features that are different, and will omit discussion of those features that are similar.

With reference to FIG. 26, the connector 650 includes a proximal body 652 having a tubular member 654 defining a lumen 656. The tubular member 654 includes a stepped exterior diameter that creates an annular shoulder 658 at a medial portion. The annular shoulder 658 faces distally. The connector 650 further includes a distal body 660 having a stepped interior diameter that creates an annular shoulder 662 at a medial portion. The annular shoulder 662 faces proximally. The annular shoulders 658, 662 form abutment surfaces that limit the travel of the proximal and distal bodies 652, 660 relative to one another.

The proximal body 652 includes a proximal collar 664 that has a similar structure to the proximal collar 572 of FIG. 22. However, the proximal collar 664 of FIG. 26 completely surrounds the distal body 660 when the connector 650 is in the disconnected closed flow configuration of FIG. 26. To open flow through the connector 650, the operator must rotate the proximal and distal bodies 652, 660 relative to one another. Since the proximal collar 664 covers the distal body 660, it is difficult for the operator to induce such relative rotation, since the distal body 660 is relatively inaccessible. Advantageously, it is thus very difficult for an operator to inadvertently open flow through the connector 650 without connecting it to a female connector, as described below.

At its distal end 666, the tubular member 654 includes an opening 668 in its sidewall. The opening 668 comprises an outlet 668 of the lumen 656. The distal body 660 includes a nozzle 670 extending distally from a proximal wall 672 of a distal collar 674. At its distal end 676, the nozzle 670 includes an opening 678 in its sidewall. The opening 678 comprises a vent 678. Adjacent the vent 678, an exterior surface of the nozzle 670 includes a recess 680 that receives a porous membrane 682. When the connector 650 is in the disconnected closed flow configuration of FIG. 26, the vent 678 is aligned with the outlet 668, enabling the connector 650 to be primed. To prime the connector 650, the operator substantially follows the steps outlined above with respect to the connectors 350, 400 of FIGS. 17 and 18. Air is forced through the lumen 656, out the outlet 668, through the opening 678 and the porous membrane 682 and through the recess 680 to the ambient atmosphere.

FIG. 27 illustrates the connector 650 connected to a female connector 684 in an open flow configuration. The process for connecting the male connector 650 and the female connector 684 is similar to the first technique described above for connecting the male connector 550 of FIGS. 22-24 to the female connector 606. Advantageously, in the illustrated embodiment the nozzle 670 includes a male taper 686 on its external surface and the female connector 684 includes a female taper 688 on its internal surface. Thus, when the female connector 684 advances sufficiently into the annular space 690 between the distal collar 674 and the nozzle 670, the nozzle external surface 686 and the female connector internal surface 688 snugly engage one another. In this configuration the female connector internal surface 688 covers and seals the vent 668 at the distal end 676 of the nozzle 670. The female connector 684 thus resists liquid leakage through the vent 668 during fluid transfer from the male connector 650 to the female connector 684.

With reference to FIG. 27, the longitudinal passageway 692 in the nozzle 670 includes a reduced diameter portion 694 located proximally of the lumen outlet 668. The reduced diameter portion 694 snugly engages the exterior of the tubular member 654 to provide a seal. The seal resists backflow of liquid through the annular space 696 between the longitudinal passageway 692 and the tubular member 654, thereby reducing the likelihood of leakage out of the connector 650.

With continued reference to FIG. 27, the proximal collar 664 includes in inwardly extending annular flange 698 in a medial portion. The distal body 660 similarly includes in outwardly extending annular flange 700 in a medial portion. The proximal collar flange 698 is located distally of the distal body flange 700 and has a smaller inner diameter than an outer diameter of the distal body flange 700. The proximal collar flange 698 thus provides an abutment surface for the distal body flange 700. When the operator moves the connector 650 from a closed flow configuration to an open flow configuration such that the proximal and distal bodies 652, 660 move away from one another, eventually the flanges 698, 700 contact one another. At that point, the operator notices a sharp increase in the amount of force necessary to continue twisting the bodies 652, 660 relative to one another. He or she then knows that the connector 650 is in the open flow configuration. The flanges 698, 700 thus reduce the likelihood of accidental axial separation of the proximal and distal bodies 652, 660.

Figure 28:
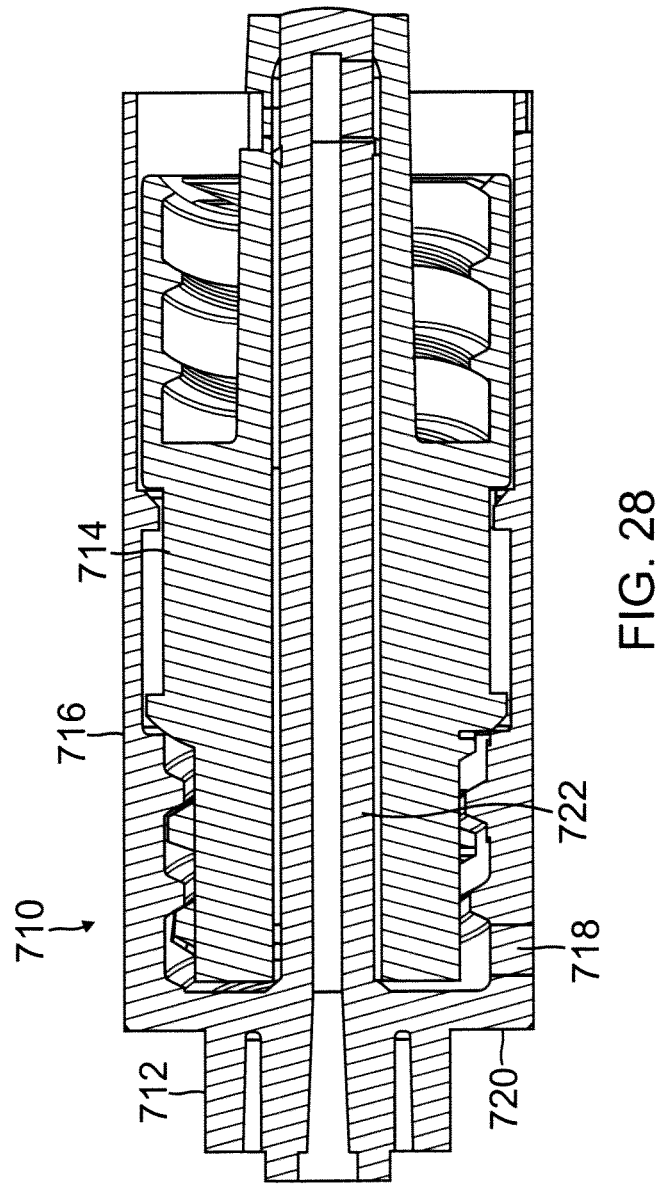
FIG. 28 is a side cross-sectional view of another embodiment of the present selectively sealable male needleless connector.

FIG. 28 illustrates another embodiment of the present selectively sealable male needleless connector 710. The connector 710 combines many of the features of the connectors 550, 650 described above and shown in FIGS. 22 and 26, as will be readily apparent to those of ordinary skill in the art. Accordingly, the description herein will focus on those features that are different, and will omit discussion of those features that are similar.

The connector 710 includes a proximal body 712 and a distal body 714 rotatable and translatable with respect to one another. The connector 710 further includes a sealing lip 715 located in the annular space 717 between the tubular member 722 and the nozzle 719. The sealing lip 715 is located just proximal of the vent 721, and resists backflow of liquid within the annular space 717. The sealing lip 715 thus reduces the volume of liquid that could collect within the connector 710.

A proximal collar 716 of the proximal body 712 includes a radial through hole 718 located adjacent a proximal end 720 of the proximal collar 716. The through hole 718 comprises a window 718 that enables an operator of the connector 710 to see the distal body 714 when the connector 710 is in the closed flow configuration of FIG. 28. When the connector 710 is in the open flow configuration (not shown), the distal body 714 is displaced distally with respect to the proximal body 712 and the distal body 714 does not appear in the window 718. Rather, the operator sees the tubular member 722 of the proximal body 712. The window 718 thus enables the operator determine whether the connector 710 is the closed flow configuration or the open flow configuration simply by looking through the window 718. In certain embodiments, the proximal body 712 and the distal body 714 may be constructed of materials of contrasting color to further aid the operator in determining whether the distal body 714 is visible through the window 718.

Figure 29:
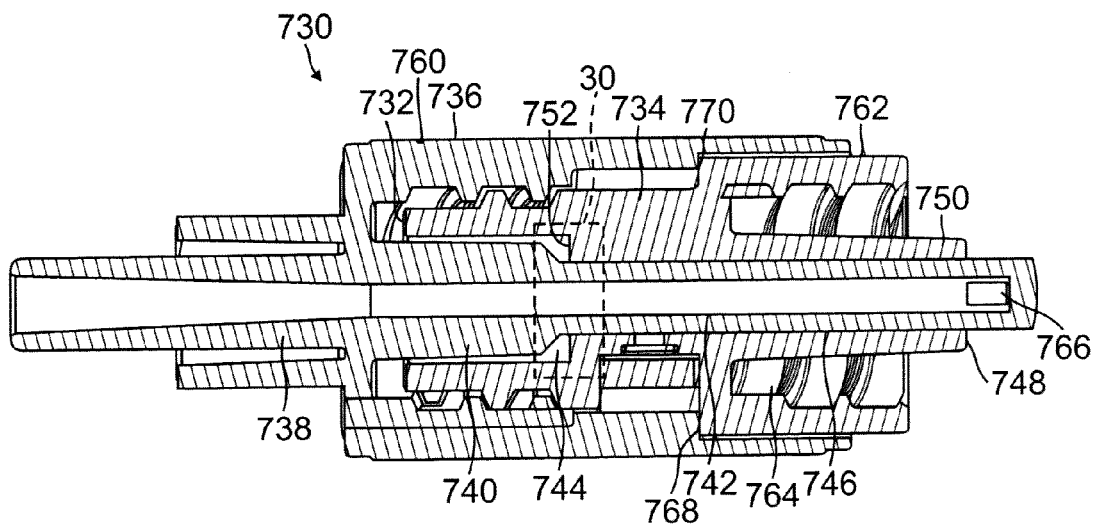
FIG. 29 is a side cross-sectional view of another embodiment of the present selectively sealable male needleless connector.

FIG. 29 illustrates another embodiment of the present selectively sealable male needleless connector 730. The connector 730 is similar in many respects to the connector 550 described above and shown in FIG. 22. Accordingly, the description herein will focus on those features that are different, and will omit discussion of those features that are similar.

In contrast to the connector 550 of FIG. 22, the connector 730 of FIG. 29 does not include an elastomeric sealing member at a proximal end 732 of its distal body 734. Rather, the proximal body 736 includes a tubular member 738 having a variable outside diameter. In a medial region, the tubular member 738 has a first diameter 740 that tapers down at approximately forty-five degrees to a second smaller diameter 742. The distal body 734 includes a proximal cavity 744 that receives the first larger diameter portion 740. The proximal cavity 744 steps down to a longitudinal passageway 746 that continues to a distal end 748 of the nozzle 750. The step down creates an annular shoulder 752.

Figure 30:
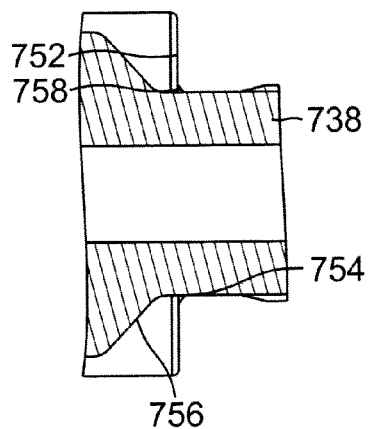
FIG. 30 is a detail view of the portion of FIG. 29 indicated by the box labeled 30.

Just distal of the annular shoulder 752, the longitudinal passageway 746 includes a reduced diameter portion 754 that forms a seal against an outer surface of the tubular member 738. The seal is shown in detail in FIG. 30, which is a detail view of the portion of FIG. 29 indicated by the box labeled 30. In certain embodiments, the seal may be enhanced by advancing the tubular member 738 such that the tapered portion 756 contacts the inner edge 758 of the annular shoulder 752. In alternative embodiments the reduced diameter portion 754 may be omitted and the seal may be created solely by abutting contact of the tapered portion 756 and the inner edge 758 of the annular shoulder 752.

Also in contrast to the connector 550 of FIG. 22, the connector 730 of FIG. 29 does not include oppositely directed threads in the proximal collar 760 and the distal collar 762. Rather, both collars 760, 762 are threaded in the same direction. Thus, when the connector 730 is in the closed flow configuration, the connector 730 is elongated from the configuration shown in FIG. 29. The connector 730 of FIG. 29 is secured to a female connector (not shown) in a similar manner as the connector 550 of FIG. 22, except that when the female connector stops advancing into the annular space 764 relative rotation of the bodies 734, 736 begins and the distal body 734 advances into the proximal collar 760, rather than backing out of it. As the distal body 734 advances into the proximal collar 760, the tubular member 738 advances out the end of the nozzle 750, rather than withdrawing farther into the nozzle 750. As the tubular member 738 advances, an opening 766 in its sidewall advances past the distal end 748 of the nozzle 750, opening fluid flow from the male connector 730 into the female connector 730. The distal body 734 stops advancing into the proximal collar 760 when a proximal facing annular shoulder 768 on the distal collar 762 contacts a distal facing annular shoulder 770 on the proximal collar 760.

Figure 31:
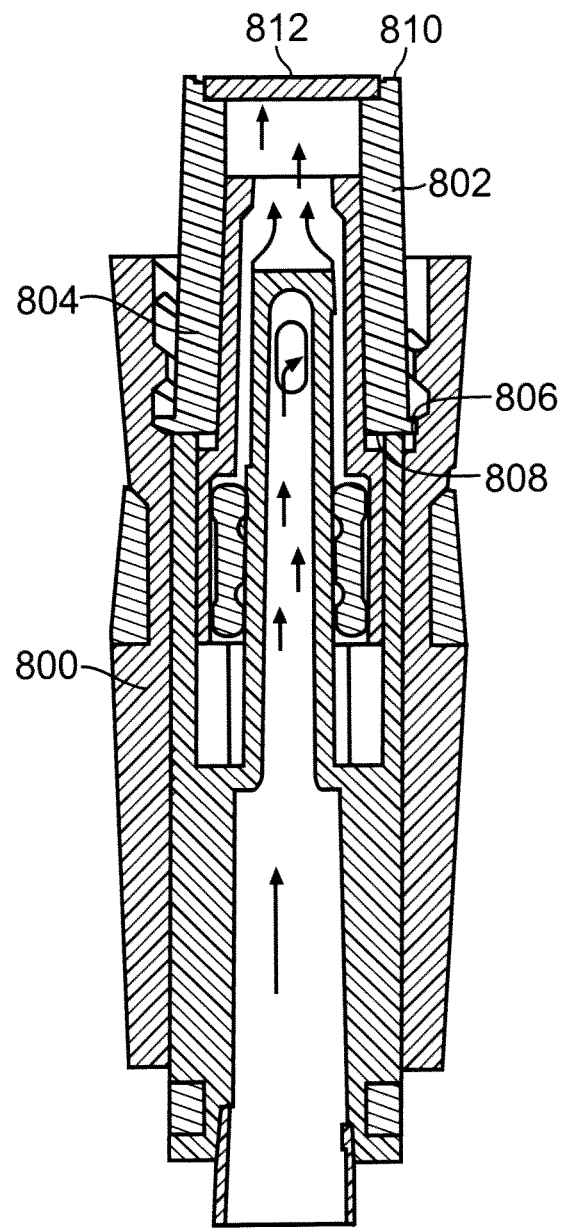
FIG. 31 is a side cross-sectional view of a male connector including a priming device.

FIG. 31 is a side cross-sectional view of a male connector 800 including a priming cap 802. The priming cap 802 includes a substantially cylindrical tapered body 804 having an external thread 806 at a distal end 808. At a proximal end 810, the cap 802 includes a hydrophobic porous membrane 812 that enables air to pass but not liquid. Screwing the cap 802 onto the connector 800, the operator can prime the connector 800 by holding it at an elevation lower than a source of IV liquid (not shown). When the cap 802 is removed, the connector 800 automatically closes.

Figure 32:
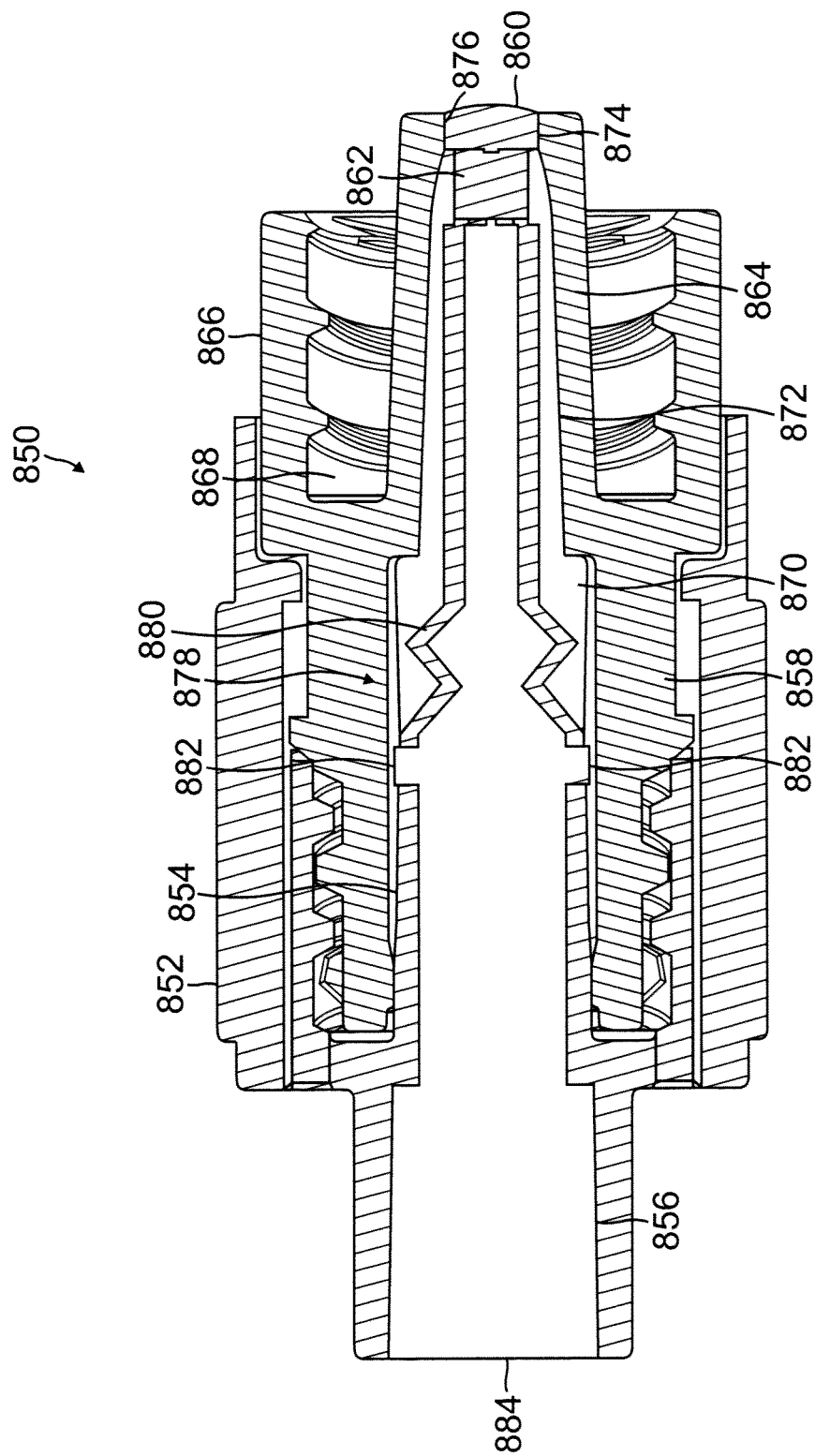
FIG. 32 is a side cross-sectional view of another embodiment of the present selectively sealable male needleless connector.
Figure 33:
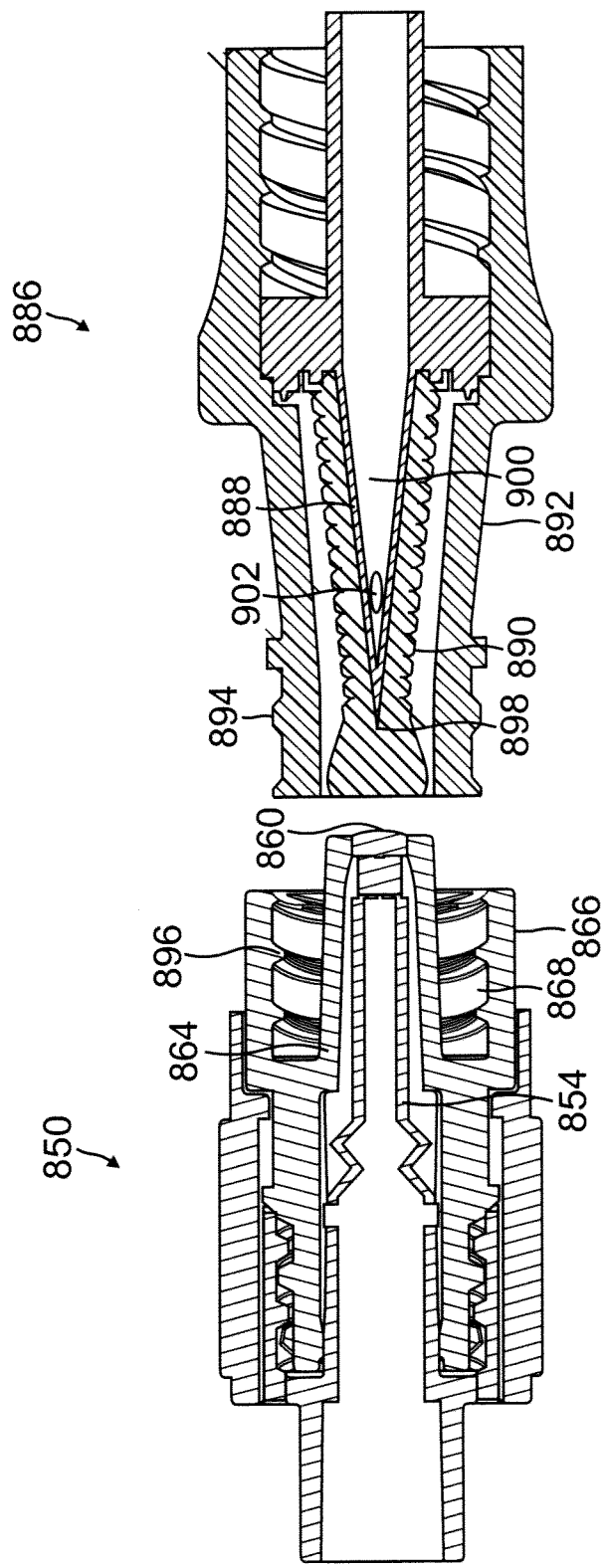
FIG. 33 is a side cross-sectional view of the connector of FIG. 32 and a female connector.

FIGS. 32 and 33 illustrate another embodiment of the present selectively sealable male needleless connector 850. The connector 850 is similar in many respects to the connector 650 described above and shown in FIGS. 26 and 27 as well as in other figures and described elsewhere herein. Accordingly, the description herein will focus on those features that are different, and will omit discussion of those features that are similar.

With reference to FIG. 32, the connector 850 includes a proximal body 852 having a tubular member 854 defining a lumen 856. The connector 850 further includes a distal body 858 that is at least partially received within the proximal body 852 and rotatable with respect to the proximal body 852. The proximal and distal bodies 852, 858 translate relative to one another when they are relatively rotated due to the incorporated threaded engagement relationship between the two, as described above with respect to the connector 650 of FIGS. 26 and 27.

Just proximal of its distal face 860, the tubular member 854 includes at least one opening 862 in its sidewall. The opening 862 comprises an outlet 874 of the lumen 856 and provides an outlet flow when the proximal and distal bodies relatively translate. A cylindrical nozzle 864 extends distally from the distal body 858. A distal collar 866 of the distal body 858 partially surrounds the nozzle 864 with an annular space 868 defined in between. The distal body 858 includes a central longitudinal passageway 870 that receives the tubular member 854. The interior diameter of the longitudinal passageway 870 is greater than the exterior diameter of the tubular member 854. The longitudinal passageway 870 and the tubular member 854 thus define an annular space 872 between them. In the illustrated embodiment, the interior diameter of the longitudinal passageway 870 tapers inwardly toward the outlet end 874 of the nozzle 864. The cross-sectional area of the annular space 872 thus decreases toward the outlet end 874 of the nozzle 864. However, those of ordinary skill in the art will appreciate that the annular space 872 could have a constant cross-sectional area over its entire length, or at least a portion of its length.

At the distal end 876 of the longitudinal passageway 870, the nozzle 864 includes a reduced interior diameter that substantially corresponds to the exterior diameter of the tubular member 854, thus forming a liquid tight seal around the tubular member 854 at the distal end. The reduced interior diameter 876 is positioned distally of the outlet 874 in the tubular member 854, so that the lumen 856 is in fluid communication with the annular space 872 through the opening 862. However, liquid in the annular space 872 does not leak out the distal end of the nozzle 864, due to the seal formed around the distal end of the tubular member 854 by the reduced interior diameter 872.

The tubular member 854 includes a longitudinally compressible section, also referred to as an accordion section 878. The accordion section 878 includes pleats 880 that compress when a proximally directed force is applied to the distal face 860 of the tubular member 854. The proximally directed force thus moves the tubular member 854 proximally with respect to the nozzle 864 by compressing the accordion section. When the tubular member 854 moves sufficiently to disengage the sealing contact between the exterior of the distal end of the tubular member 854 and the interior of the distal end of the nozzle 864, liquid within the connector 850 may flow out of the connector 850 through the distal end of the nozzle 864. The accordion section 878 thus facilitates compatibility between the connector 850 and a female connector that includes an interior spike 888 or post, as described in further detail below. However, the connector 850 is equally adaptable for use with a female Luer connector that does not incorporate a stationary spike or post.

The proximal and distal bodies 852, 858 may be formed of any durable material that is also rigid or semi-rigid, such as a plastic. However, at least the proximal body 852 may be formed of a material that provides at least a moderate amount of flexibility when a wall thickness of the material is relatively thin. In one embodiment, for example, the proximal body 852 may be formed of polypropylene. The flexibility facilitates compression of the accordion section 878 when a proximally directed force is applied to the distal end of the tubular member 854.

Just proximal of the accordion section 878, the tubular member 854 includes at least one opening 882 comprising a lateral fluid passage. The lateral fluid passages 882 fluidly connect the lumen 856 with the annular space 872. Thus, fluid entering the connector 850 from the proximal end 884 flows through the lumen 856. A portion of the fluid passes through the lateral fluid passages 882 into the annular space 872, and fluid continues to flow distally through both the lumen 856 and the annular space 872 toward the outlet 874. The co-flow configuration of the lumen 856 and the annular space 872 eliminates dead spaces in the connector 850 where fluid may collect and stagnate. Fluid flowing through the lumen 856 and the annular space 872 flushes out fluid that flowed through previously. The lack of fluid stagnation reduces the likelihood that pathogens may grow within the connector 850, thereby reducing the likelihood of infecting the person to whom the fluid flows. Thus, an aspect of the present embodiment is understood to include a connector having tubular member located inside a distal body and wherein fluid flowing through the tubular member is discharged through a central flow path and an annular flow path. In a specific aspect of the present embodiment, a multi-flow path male connector is provide in which fluid is configured to flow through a tubular section and out a distal opening and out a lateral opening and into an annular flow space.

The connector 850 of FIG. 32 is configured to matingly connect with a female connector, such as the female connectors 30, 606, 684 described above with respect to the previous embodiments. The procedure for connecting the connector 850 of FIG. 32 to a female connector is similar to that described above with respect to FIGS. 26 and 27. If the female connector includes an internal sealing member 122 (FIG. 3), the nozzle 864 and the tubular member 854 compress the sealing member 122 to open the slit 84 therein as the male and female connectors are screwed onto one another. A similar opening progression is described above with respect to FIGS. 3-5.

The connector 850 of FIG. 32 is also configured to matingly connect with a female connector 886 that includes an interior spike or post in addition to a sealing member 890 having a slit. FIG. 33 illustrates the connector 850 and a commercially available female connector 886 including an interior spike 888 surrounded by a sealing member 890. The female connector 886 includes a cylindrical housing 892 having exterior threads 894. The housing 892 is configured to be received within the annular space 868 between the distal collar 866 and the nozzle 864. The threads 894 on the female connector 886 are configured to engage the threads 896 on the interior of the distal collar 866 to advance the male and female connectors 850, 886 toward one another as they are relatively rotated. However, before the threads 894, 896 can engage one another, the protruding distal ends of the nozzle 864 and the tubular member 854 are pushed into the interior of the housing 892. The advancing nozzle 864 and tubular member 854 compress the sealing member 890 and force it distally into the housing 892. A slit (not shown) in the sealing member 890 opens as the sealing member 890 is forced distally.

When the nozzle 864 and tubular member 854 advance far enough, a tip 898 of the spike 888 contacts the distal face 860 of the tubular member 854. The spike 888 is fixed in its longitudinal position relative to the housing 892. Thus, after the tip 898 of the spike 888 contacts the distal face 860, the operator continues to advance the nozzle 864 into the housing 892, but the spike 888 prevents further advancement of the tubular member 854. The spike 888 thus forces the tubular member 854 proximally relative to the nozzle 864 by compressing the accordion section of the tubular member. Eventually, the exterior surface of the distal end of the tubular member 854 disengages the interior surface of the distal end of the nozzle 864, opening 862 fluid flow out the nozzle 864. The disengagement may occur before or after the threads 894, 896 on the connectors 850, 886 engage one another. Once the threads 894, 896 do engage, the operator further advances the connectors 850, 886 toward one another through relative twisting, similarly as described above with respect to the previous embodiments. The outlet 874 may also close by reversing the relative twisting between the proximal body 852 and the distal body 858 without completely disconnecting the female connector 886 from the distal body. Thus, an aspect of the present embodiment is understood to include a connector configured for use with a female Luer connector having a spike or a post and wherein the fluid flow between the connector and the female Luer connector may open or close without having to physically disconnect the female Luer connector from the connector. A further feature of the connector is the ability to connect to a female Luer connector that does not incorporate a spike or a post.

Fluid flowing out the nozzle 864 may flow into the hollow interior 900 of the spike 888 through an aperture 902 in the wall of the spike 888 located distally of the spike 888 tip 898. The illustrated female connector 886 is only one example of a commercially available connector with which the present connector 850 is compatible. Other female connectors may include a post having a blunt end, rather than the pointed tip 898 of the spike 888.

The above description presents the best mode contemplated for carrying out the present selectively sealable male needleless connector, and of the manner and process of making and using it, in such full, clear, concise, and exact terms as to enable any person skilled in the art to which it pertains to make and use this connector. This connector is, however, susceptible to modifications and alternate constructions from that discussed above that are fully equivalent. Consequently, this connector is not limited to the particular embodiments disclosed. On the contrary, this connector covers all modifications and alternate constructions coming within the spirit and scope of the connector as generally expressed by the following claims, which particularly point out and distinctly claim the subject matter of the connector. For example, features or structures specially discussed for one embodiment may be used or incorporated in another embodiment provided the function or purpose is compatible.

What is claimed is:

1. A male needleless connector, comprising:
   a body defining a first portion of a fluid pathway;
   a tubular member extending in a distal direction away from the first portion and defining a second portion of the fluid pathway that when used with a female needleless connector is closer to the female needleless connector than the first portion, the tubular member including a fluid opening at its distal end;
   a collar at least partially surrounding the tubular member, the collar having internal threads to threadably engage with external threads of the female needleless connector and having external threads to threadably engage with internal threads of the body; and
   a sealing member at least partially surrounding the tubular member and being translatable relative to the tubular member;
   wherein the connector includes a closed configuration and an open configuration, the open configuration defined by rotation of the external threads of the collar relative to the internal threads of the body in a first direction and the closed configuration defined by rotation of the external threads of the collar relative to the internal threads of the body in a second direction, which is opposite the first direction, and in the closed configuration the sealing member covers the fluid opening and in the open configuration the sealing member permits fluid flow through the fluid opening.

2. The connector of claim 1, wherein the sealing member is biased toward the closed configuration.

3. The connector of claim 1, wherein the collar overlaps the body and is rotatable with respect to the body.

4. The connector of claim 1, wherein the collar overlaps the body and is translatable with respect to the body.

5. The connector of claim 1, wherein the body includes an annular channel on its outer surface, the collar includes at least one boss on its inner surface, and the boss seats within the channel.

6. The connector of claim 1, wherein the tubular member comprises a pleated section and an opening proximal of the fluid opening.

7. The connector of claim 1, further comprising a porous membrane in fluid communication with the fluid pathway, the porous membrane being configured to allow gaseous particles to pass through the membrane and to block liquid particles from passing through the membrane.

8. The connector of claim 1, wherein the sealing member includes a pressure valve configured to halt fluid flow through the sealing member in response to a pressure buildup within the sealing member.

9. A male connector, comprising:
   a first body comprising an elongated tubular member and a collar partially surrounding the elongated tubular member, the elongated tubular member defining a fluid pathway, the collar having internal threads; and
   a second body translatable relative to the first body comprising a longitudinal passageway surrounding the elongated tubular member and a collar partially surrounding the longitudinal passageway, the longitudinal passageway having external threads threadably engaging the internal threads of the collar of the first body, the collar of the second body having internal threads configured to threadably engage with external threads of a female connector;
   wherein a seal is formed between the elongated tubular member and the longitudinal passageway, and the seal unseals when the first body is rotated relative to the second body.

10. The male connector of claim 9, wherein an end of the longitudinal passageway has a reduced interior diameter, and the seal is formed between the elongated tubular member and the reduced interior diameter of the longitudinal passageway.

11. The male connector of claim 9, wherein the threaded engagement between the collar of the first body and the longitudinal passageway produces relative translation between the first body and the second body when rotated with respect to one another.

12. The male connector of claim 9, further comprising a porous membrane in fluid communication with the lumen, the porous membrane being configured to allow gaseous particles to pass through the membrane and to block liquid particles from passing through the membrane.

13. The connector of claim 9, wherein the sealing member includes a pressure valve configured to halt fluid flow through the sealing member in response to a pressure buildup within the sealing member.

14. The connector of claim 9, further comprising a sealing member located between an opening of the longitudinal passageway and threaded engagement between the collar of the first body and the longitudinal passageway.

15. The connector of claim 9, wherein a first opening of the fluid pathway of the elongated tubular member is configured to couple with a tubing.

16. The connector of claim 15, wherein a second opening of the fluid pathway is defined adjacent a distal/second end of the elongated tubular member.

* * * * *

UNITED STATES PATENT AND TRADEMARK OFFICE
CERTIFICATE OF CORRECTION

PATENT NO. : 8,910,919 B2  
APPLICATION NO. : 13/392642  
DATED : December 16, 2014  
INVENTOR(S) : Olivier Bonnal Page 1 of 1

It is certified that error appears in the above-identified patent and that said Letters Patent is hereby corrected as shown below:

In the Specification

In column 1, line 67, delete "being," and insert -- being --, therefor.

In column 3, line 15, delete "connector:" and insert -- connector; --, therefor.

In column 3, line 40, delete "connector:" and insert -- connector; --, therefor.

In column 3, line 48-49, delete "connector:" and insert -- connector; --, therefor.

In column 3, line 63-64, delete "connector:" and insert -- connector; --, therefor.

In column 4, line 21, delete "FIG. 22:" and insert -- FIG. 22; --, therefor.

In column 8, line 20, delete "polyvinyldiflouride" and insert -- polyvinyldifluoride --, therefor.

In column 16, line 24, delete "passageway's" and insert -- passageways --, therefor.

In column 32, line 6, delete "matingly" and insert -- mattingly --, therefor.

In column 32, line 18-19, delete "matingly" and insert -- mattingly --, therefor.

Signed and Sealed this  
Twenty-first Day of July, 2015

Michelle K. Lee  
*Director of the United States Patent and Trademark Office*